US009526778B2

(12) United States Patent
Alonso et al.

(10) Patent No.: US 9,526,778 B2
(45) Date of Patent: Dec. 27, 2016

(54) INFLUENZA VACCINE, COMPOSITION, AND METHODS OF USE

(75) Inventors: Sylvie Alonso, Singapore (SG); Rui Li, Singapore (SG); Vincent Chow, Singapore (SG); Camille Locht, Lille (FR)

(73) Assignees: Institut Pasteur de Lille, Lille (FR); Institut National de la Sante et de la Recherche Medicale, Paris (FR); National University of Singapore, Singapore (SG)

( * ) Notice: Subject to any disclaimer, the term of this patent is extended or adjusted under 35 U.S.C. 154(b) by 0 days.

(21) Appl. No.: 13/377,070

(22) PCT Filed: Jun. 15, 2009

(86) PCT No.: PCT/IB2009/007153
§ 371 (c)(1),
(2), (4) Date: Feb. 2, 2012

(87) PCT Pub. No.: WO2010/146414
PCT Pub. Date: Dec. 23, 2010

(65) Prior Publication Data
US 2012/0121647 A1    May 17, 2012

(51) Int. Cl.
| | |
|---|---|
| *A61K 39/145* | (2006.01) |
| *A61K 39/00* | (2006.01) |
| *A61K 39/10* | (2006.01) |
| *A61K 39/02* | (2006.01) |
| *A61K 39/12* | (2006.01) |

(52) U.S. Cl.
CPC ........... *A61K 39/145* (2013.01); *A61K 39/099* (2013.01); *A61K 39/12* (2013.01); *A61K 2039/521* (2013.01); *A61K 2039/522* (2013.01); *A61K 2039/523* (2013.01); *A61K 2039/543* (2013.01); *A61K 2039/55566* (2013.01); *A61K 2039/58* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 6,713,072 B1 | 3/2004 | Pizza et al. | |
| 6,841,358 B1 | 1/2005 | Locht et al. | |
| 2005/0147607 A1 | 7/2005 | Reed | |
| 2009/0246222 A1 | 10/2009 | Locht et al. | |
| 2010/0111996 A1* | 5/2010 | Leclerc | 424/202.1 |

FOREIGN PATENT DOCUMENTS

| | | |
|---|---|---|
| WO | 9816553 | 4/1998 |
| WO | WO 03/102170 | 12/2003 |
| WO | WO 2007/104451 | 9/2007 |
| WO | WO 2008/156753 | 12/2008 |
| WO | WO 2010/125014 | 11/2010 |

OTHER PUBLICATIONS

Edenborough et al. J. Virology 86: 12544-12551, Sep. 5, 2012.*
Fiers et al. Virus Res. 103: 173-176, 2004.*
Alonso, S. et al., "Production of Nontypeable *Haemophilus influenzae* HtrA by Recombinant *Bordetella pertussis* with the Use of Filamentous Haemagglutinin as Carrier," *Infection and Immunity*, Jul. 2005, pp. 4295-4301, vol. 73, No. 7.
Budapest Treaty on the International Recognition of the Deposit of Microorganisms for the Purposes of Patent Procedure, Bordatella pertussis BPLR6, Accession No. V09/009169, Apr. 30, 2009, one page.
Carbonetti, N. H., "Immunomodulation in the Pathogenesis of *Bordetella pertussis* Infection and Disease," *Current Opinion in Pharmacology*, Jun. 2007, pp. 272-278, vol. 7, No. 3.
Child Innovac, European Network on Nasal Vaccination against Respiratory Infections in Young Children, Date Unknown, six pages. [Online] [Retrieved Jun. 16, 2012] Retrieved from the Internet <URL:http://www.child-innovac.org/Child-Innovac_Leaflet.pdf.>.
Coppens, I. et al., "Production of *Neisseria meningitidis* Transferrin-Binding Protein B by Recombinant Bordetella pertussis," *Infection and Immunity*, Sep. 2001, pp. 5440-5446, vol. 69, No. 9.
Ennis, D. et al., "Prior *Bordetella pertussis* Infection Modulates Allergen Priming and the Severity of Airway Pathology in a Murine Model of Allergic Asthma," *Clinical and Experimental Allergy*, Sep. 2004, pp. 1488-1497, vol. 34, No. 9.
Ennis, D. et al., "Whole-cell Pertussis Vaccine Protects against *Bordetella pertussis* Exacerbation of Allergic Asthma," *Immunology Letters*, Feb. 15, 2005, pp. 91-100, vol. 97, No. 1.
Feunou, P.F. et al., "Genetic Stability of the Live Attenuated Bordetella pertussis Vaccine Candidate BPZE1," *Vaccine*, 2008, pp. 5722-5727, vol. 26, Issue 45.
Higgins, S.C. et al., "Toll-like Receptor 4-mediated Innate IL-10 Activates Antigen-Specific Regulatory T Cells and Confers Resistance to *Bordetella pertussis* by Inhibiting Inflammatory Pathology," *Journal of Immunology*, Sep. 2003, pp. 3119-3127, vol. 171, No. 6.
Ho, S. Y. et al., "Highly Attenuated *Bordetella pertussis* Strain BPZE1 as a Potential Live Vehicle for Delivery of Heterologous Vaccine Candidates," *Infection and Immunity*, Jan. 2008, pp. 111-119, vol. 76, No. 1.
Kavanagh, H. et al., "Attenuated *Bordetella pertussis* Vaccine Strain PBZE1 Modulates Allergen-induced immunity and Prevents Allergic Pulmonary Pathology in a Murine Model," *Clinical and Experimental Allergy*, Jun. 2010, pp. 933-941, vol. 40, No. 6.

(Continued)

*Primary Examiner* — S. Devi
(74) *Attorney, Agent, or Firm* — Stanley A. Kim

(57) ABSTRACT

The invention relates to compositions and vaccines that include a mutated *Bordetella* strain for treating or preventing an influenza infection in a mammal. In addition, the invention further provides methods for protecting a mammal against infection by influenza and/or eliciting an immune response against an influenza virus in a mammal using the composition or vaccine.

6 Claims, 8 Drawing Sheets

(56) References Cited

OTHER PUBLICATIONS

Martignon, G. et al., "Does Childhood Immunization against Infectious Diseases Protect from the Development of Atopic Disease?," *Pediatric Allergy and Immunology*, May 2005, pp. 193-200, vol. 16, No. 3.

Mattoo, S. et al., "Mechanisms of *Bordetella* Pathogenesis," *Frontiers in Bioscience* 6, Nov. 2001, pp. e168-e186, vol. 6.

Mattoo, S. et al., "Molecular Pathogenesis, Epidemiology, and Clinical Manifestations of Respiratory Infections Due to *Bordetella pertussis* and other *Bordetella* Subspecies," *Clinical Microbiology Reviews*, Apr. 2005, pp. 326-382, vol. 18, No. 2.

McGuirk, P. et al., "Pathogen-specific T Regulatory 1 Cells Induced in the Respiratory Tract by a Bacterial Molecule that Stimulates Interleukin 10 Production by Dendritic Cells: A Novel Strategy for Evasion of Protective T Helper Type 1 Responses by *Bordetella pertussis*," *Journal of Experimental Medicine*, Jan. 21, 2002, pp. 221-231, vol. 195, No. 2.

Menozzi, F.D. et al., "Identification and Purification of Transferrin- and Lactoferrin-Binding Proteins of *Bordetella pertussis* and *Bortdetall bronchiseptica*," *Infection and Immunity*, Nov. 1991, pp. 3982-3988, vol. 59, No. 11.

Mielcarek, N. et al., "Attenuated *Bordetella pertussis*: New Live Vaccines for Intranasal Immunization," *Vaccine*, Apr. 2006, pp. S54-S55, vol. 24, Supplement 2.

Mielcarek, N. et al., "Intranasal Priming with Recombinant *Bordetella pertussis* for the Induction of a Systemic Immune Response Against a Heterologous Antigen," *Infection and Immunity*, 1997, pp. 544-550, vol. 65, No. 2.

Mielcarek, N. et al., "Live Attenuated B. pertussis as a Single-Dose Nasal Vaccine Against Whooping Cough," *PLoS Pathogens*, Jul. 2006, pp. 0662-0670, vol. 2, Issue 7.

Mielcarek, N. et al., "Nasal Vaccination Using Live Bacterial Vectors," *Advanced Drug Delivery Reviews*, Sep. 2001, pp. 55-69, vol. 51.

Narasaraju, T. et al., "Adaptation of Human Influenza H3N2 Virus in a Mouse Pneumonitis Model: Insights into Viral Virulence, Tissue Tropism and Host Pathogenesis," *Microbes and Infection*, Jan. 2009, pp. 2-11, vol. 11, No. 1.

Pascal, F., "T.119.T-but not B-Cell-Mediated Protection Induced by Nasal Administration Using Live Attenuated Bordetella pertussis BPZE1 Cross Protect Against B.Parapertussis," *Clinical Immunology*, p. S86, vol. 131, Supplement 1, 2009.

PCT Indications Relating to the Deposited Microorganism or Other Biological Material, Collection Nationale de Cultures de Microorganismes (CNCM), Accession No. CNCM I-3585, Mar. 9, 2009, one page.

PCT International Preliminary Report on Patentability, PCT Application No. PCT/EP2007/001942, Sep. 16, 2008, eight pages.

PCT International Search Report and Written Opinion, PCT Application No. PCT/IB2009/007153, Mar. 18, 2010, eleven pages.

PCT International Search Report and Written Opinion, PCT Application No. PCT/EP2010/055507, Jul. 6, 2010, nine pages.

Renauld-Mongenie, G. et al., "Induction of Mucosal Immune Response Against a Heterologous Antigen Fused to Filamentous Hemagglutinin after Intranasal Immunization with recombinant *Bordetella pertussis,*" *Proceedings of the Natl. Acad. Sci. USA*, Jul. 1996, pp. 7944-7949, vol. 93.

Reveneau, N. et al., "Tetanus Toxin Fragment C-specific Priming by Intranasal Infection with Recombinant *Bordetella pertussis,*" *Vaccine*, 2001, pp. 926-933, vol. 20.

Canadian Intellectual Property Office, Examination Report, Canadian Patent Application No. 2,765,364, Oct. 15, 2012, four pages.

Abe, T. et al., "Baculovirus Induces an Innate Immune Response and Confers Protection from Lethal Influenza Virus Infection in Mice," *Journal of Immunology*, 2003, pp. 1133-1139, vol. 171.

European Patent Office, Supplementary European Search Report, European Patent Application No. 09846104.9, Nov. 27, 2012, eight pages.

Marsolais, D. et al., "A critical role for the sphingosine analog AAL-R in dampening the cytokine response during influenza virus infection," *PNAS*, Feb. 3, 2009, pp. 1560-1565, vol. 106, No. 5.

Skerry, C. et al., "A Live, Attenuated *Bordetella pertussis* Vaccine Provides Long-Term Protection against Virulent Challenge in a Murine Model," Clinical and Vaccine Immunology, Feb. 2011, pp. 187-193, vol. 18, No. 2.

European Patent Office, Examination Report, European Patent Application No. 09846104.9, Jun. 27, 2013, five pages.

Canadian Intellectual Property Office, Office Action, Canadian Patent Application No. 2,765,364, Jan. 28, 2014, two pages.

European Patent Office, Examination Report, European Patent Application No. 09846104.9, Nov. 20, 2013, four pages.

Japanese Patent Office, Office Action, Japanese Patent Application No. 2012-515573, Oct. 7, 2013, seven pages.

State Intellectual Property Office of the People's Republic of China, First Office Action, Chinese Patent Application No. 200980160953. 1, Aug. 22, 2013, twenty pages.

Willems, R.J. L. et al., "The efficacy of a whole cell pertussis vaccine and fimbriae against *Bordetella pertussis* and *Bordetella parapertussis* infections in a respiratory mouse model," *Vaccine*, Feb. 1998, pp. 410-416, vol. 16, No. 4.

Zhao, Z. et al., "Protecting mice from fatal *Bordetella bronchiseptica* infection by immunization with recombinant pertactin antigens," *Acta Biologica Sinica*, Mar. 2008, pp. 337-341, vol. 48, No. 3 [with English abstract].

Yusibov, V. et al.: "Peptide-based candidate vaccine against respiratory syncytial virus," Vaccine, 2005, vol. 23:2261-2265.

Walker, K. E. et al.: "Characterization of the dermonecrotic toxin in members of the genus *Bordetella*," Infect. Immun., 1994, vol. 62, No. 9:3817-3828.

Teman, UA. et al.: "A novel role for murine IL-4 in vivo: induction of MUC5AC gene expression and mucin hypersecretion," Am J Respir Cell Mol Biol., 1997, vol. 16(4):471-478.

Stith, Rebecca et al.: "The link between tracheal cytotoxin production and peptidoglycan recycling in Bordetella Pertussis," Abstracts of the General Meeting of the American Society for Microbiology, New Orleans; 1996; vol. 96:184 (XP008013937).

Li, Rui, et. al.: "Attenuated Bordetella pertussis BPZE1 as a live vehicle for heterologous vaccine antigens delivery thorugh the nasal route," Bioengineered Bugs, 2011, vol. 2(6):315-319.

Li, Rui, et al.: "Development of live attenuated Bordetella pertussis strains expressing the universal influenza vaccine candidate M2e," Vaccine, 2011, vol. 29:L5502-5511.

Romagnani, Sergio, "Immunologic influences on allergy and the TH1/TH2 balance," J Allergy Clin Immunol, 2004, pp. 395-400.

Nemery, B. et al.: "Interstitial lung disease induced by exogenous agents: factors governing susceptibility," Eur Respir J, 2001, vol. 18, Suppl. 32:30s-42s.

Neirynck, Sabine, et al.: "A universal influenza A vaccine based on the extracellular domain of the M2 protein," Nature Medicine, 1999, vol. 5:1157-1163.

Nagel, Gabriele et al.: "Association of pertussis and measles infections and immunizations with asthma and allergic sensitization in ISAAC Phase Two, Pediatric Allergy and Immunology," 2012, vol. 23:736-745.

Morokata, T. et al.: "C57BL/6 mice are more susceptible to antigen-induced pulmonary eosinophilia than BALB/c mice, irrespective of systemic T helper 1/T helper 2 responses," Immunology, 1999, vol. 98:345-351.

Hansen, Gesine et al.: "Allergen-specific Th1 cells fail to counterbalance Th2 cell-induced airway hyperreactivity but cause severe airway inflammation," J. Clin. Invest., 1999, vol. 103:175-183.

Hamelmann, E. et al.: "Role of IgE in the development of allergic airway inflammation and airway hyperresponsiveness a murine model," Allergy, 1999, vol. 54:297-305.

Gleich, Gerald J.: "Mechanisms of eosinophil-associated inflammation," J. Allergy Clin. Immunol., 2000, pp. 651-663.

Giefing, Carmen et al.: "Discovery of a novel class of highly conserved vaccine antigens using genomic scale antigenic fingerprinting of pneumococcus with human antibodies," JEM, 2008, vol. 205(1):117-131.

(56) References Cited

OTHER PUBLICATIONS

Galli, Stephen J., et al.: "The development of allergic inflammation," Nature, 2008, vol. 454:445-454.

De Filette et al.: "Improved design and intranasal delivery of an M2e-based human influenza A vaccine," Vaccine, 2006, vol. 24, pp. 6597-6691.

Mielcarek, Nathalie et al.: "Homologous and heterologous protection after single intranasal administration of live attenuated recombinant Bordetella pertussis," Nature Biotechnology, 1998, vol. 16:454-457.

Marsland, B.J., et al.: "Allergic airway inflammation is exacerbated during acute influenza infection and correlates with increased allergen presentation and recruitment of allergen-specific T-helper type 2 cells," Clinical & Experimental Allergy, 2004, vol. 34, Issue 8.

Mahon, B., et al.: "Atypical Disease after Bordetella pertussis Respiratory Infection of Mice with Targeted Disruptions of Interferon-γReceptor or Immunoglobulin μ Chain Genes," J. Exp. Med., 1997, vol. 186, No. 11:1843-1851.

Locht, Camille, et al.: "Bordetella pertussis: from functional genomics to intranasal vaccination," Iny. J. Med. Microbiol., 2004, vol. 293:583-588.

Li, Z.M., et al.: "Cloning and sequencing of the structural gene for the porin protein of Bordetella pertussis," Molecular Biology, 1991, vol. 5 (7):1649-1656.
Li, Rui et al.: "Attenuated Bordetella pertussis Protects against Highly Pathogenic Influenza A Viruses by dampending the Cytokine Storm," Journal of Virology, 2010, vol. 84(14):7105-7113.
Laemmli, U.K.: "Cleavage of Structural Proteins during the Assembly of the Head of Bacteriophage T4," Nature, 1970, pp. 680-685.
Humbert, Marc et al.: "Elevated expression of messenger ribonucleic acid encoding IL-13 in the bronchial mucosa of atopic and nonatopic subjects with asthma," Journal of Allergy and Clinical Immunology, 1997, vol. 99 (5):657-665.
Huang, Chin Chiang, et al.: "Experimental Whooping Cough," N Engl J Med, vol. 266:105-111, 1962.
Holgate, Stephen, et al.: "The anti-inflammatory effects of omalizumab confirm the central role of IgE in allergic inflammation," J Allergy Clin Immunol, 2005, vol. 115:459-465.
Hausman, Sally Z. and Burns, Drusilla L.: "Use of Pertussis Toxin Encoded by ptx Genes from Bordetella bronchiseptica to Model the Effects of Antigenic Drift of Pertussis Toxin on Antibody Neutralization," Infect. Immun. 68: 3763-3767, 2000.

* cited by examiner

Fig. 5

INFLUENZA VACCINE, COMPOSITION, AND METHODS OF USE

FIELD

The invention relates to fields of microbiology and virology.

BACKGROUND

There are three types of influenza virus: A, B, and C, which vary greatly in their epidemiological pattern. Influenza A virus is both the best characterized and the most serious threat to public health, capable of inducing massive epidemics or pandemics. This virus is also highly variable antigenically, making effective vaccine production difficult.

A vaccine to influenza would be one of the most efficacious, safe, nontoxic, and economical weapons to prevent disease and to control the spread of the disease. The primary aim of vaccination is to activate the adaptive specific immune response, primarily to generate B and T lymphocytes against antigen(s) associated with the disease or the disease agent.

Currently some vaccines against influenza are available and primarily consist of inactivated vaccines. These vaccines can comprise two type A antigens (e.g., H1N1 and H3N2) and one type B antigen. The available vaccines typically include whole virion, split-product, and subunit vaccines. Generally, these vaccines are effective in up to 90% of vaccinated individuals if the vaccines closely match the identity of the emerging epidemic. However, they need to be updated each year to keep pace with antigenic drift of the influenza virus.

Moreover, a cold-adapted live attenuated intranasal vaccine (LAIV) against seasonal influenza has been recently described. Cross-protective immunity was demonstrated in a study which reported protection against a H3N2 virus in cotton rats infected with a H1N1 strain. However, one major concern linked with LAIV is the possibility of genetic reversion and re-assortment with wild-type influenza viruses, resulting in a new, potentially infectious strain.

The invention addresses these and other problems in the influenza vaccine field by providing a vaccine and composition that elicits an immune response against one or more influenza strains using a mutated *Bordetella* strain as the active principle agent.

In addition, the related art describes various types of vaccines and compositions using *Bordetella* strains (WO2007104451 and WO2003102170) to induce immune responses against, e.g., *Bordetella* bacteria capable of causing whooping cough in humans; however the art fails to disclose methods or compositions for eliciting an immune response to an influenza virus in a mammal using the methods, compositions, and/or vaccines of the invention.

Thus, a need exists for a novel influenza vaccine capable of providing broad protection against diseases caused by influenza virus infection.

BRIEF SUMMARY

The invention relates to compositions and vaccines that include a mutated *Bordetella* strain for treating or preventing an influenza infection in a mammal. In addition, the invention further provides methods for protecting a mammal against infection by influenza and/or eliciting an immune response against an influenza virus in a mammal using the composition or vaccine.

In one aspect, the invention provides a method of eliciting an immune response against an influenza virus in a mammal, comprising: administering a mutated *Bordetella* strain to the mammal, wherein the strain comprises a mutated pertussis toxin (ptx) gene, a deleted or mutated dermonecrotic (dnt) gene, and a heterologous ampG gene. In some aspects, the *Bordetella* strain comprises a *Bordetella pertussis* strain. In some such aspects, the wild-type *Bordetella* strain ampG gene is replaced by an *E. Coli* ampG gene. In other aspects, the mutation of the ptx gene comprises the substitution of an amino acid involved in substrate binding and/or an amino acid involved in catalysis. In some such aspects, the substitution of the amino acid involved in substrate binding comprises R9K and the substitution of the amino acid involved in catalysis comprises E129G. In some aspects, the *Bordetella* strain comprises a triple mutant strain. In some such aspects, the *Bordetella* strain comprises a BPZE1 strain. In other such aspects, the *Bordetella* strain is attenuated. In some aspects, the *Bordetella* strain comprises a live strain. In other aspects, the *Bordetella* strain does not comprise a heterologous gene other than the heterologous ampG gene. In some aspects, the *Bordetella* strain does not comprise a heterologous expression platform to carry heterologous antigens to the respiratory mucosa of the mammal. In other aspects, the methods further comprise the prevention or treatment of the influenza infection in the mammal. In some aspects, the *Bordetella* strain is administered prior to the influenza infection. In some such aspects, the *Bordetella* strain is administered about 6 weeks or more prior to the influenza infection. In other such aspects, the *Bordetella* strain is administered about 12 weeks or more prior to the influenza infection. In some aspects, the influenza virus comprises H3 or H1. In other aspects, the influenza virus comprises N2 or N1.

In some aspects, the influenza virus comprises H3 and N2. In other aspects, the influenza virus comprises H1 and N1. In some aspects, the immune response comprises a Th1 immune response. In some aspects, the strain is administered to the mammal by subcutaneous (s.c.), intradermal (i.d.), intramuscular (i.m.), intravenous (i.v.), oral, or intranasal administration; or by injection or by inhalation. In other aspects, the strain is administered intranasally. In some other aspects, the strain is administrated to a mammal in need of protective immunity against the influenza infection. In some aspects the mammal is a child. In some aspects, the strain is administered once in a single dose. In some aspects, the strain is administered in more than one dose. In some such aspects, the strain is administered twice in two doses. In other aspects, the two doses are administered about 3 weeks apart. In some aspects, a level of protection against the influenza infection is more than about 60%. In other aspects, a level of protection against the influenza infection is more than about 50%. In some aspects, the mammal is a human.

In another aspect, the invention provides methods of eliciting a protective immune response against an H3N2 influenza virus in a human, comprising: intranasally administering a live and attenuated BPZE1 strain to the human prior to infection of the human by the H3N2 influenza virus, wherein the strain does not comprise a heterologous expression platform to carry heterologous antigens to the respiratory mucosa of the human.

In another aspect, the invention provides methods of eliciting an immune response against an influenza virus in a human, comprising: administering a live *Bordetella* strain to the human, wherein the strain does not comprise a heterologous expression platform to carry heterologous antigens to the respiratory mucosa of the human.

In another aspect, the invention provides methods of protecting a mammal against a disease caused by an influenza infection, comprising: administering to the mammal a mutated *Bordetella* strain comprising a mutated ptx gene, a deleted or mutated dnt gene, and a heterologous ampG gene.

In another aspect, the invention provides a protective immunity against an influenza infection, comprising: administering to the mammal a mutated *Bordetella* strain comprising a mutated ptx gene, a deleted or mutated dnt gene, and a heterologous ampG gene.

In another aspect, the invention provides a composition for treating or preventing an influenza infection in a mammal, comprising: a mutated *Bordetella* strain, wherein the strain comprises a mutated pertussis toxin (ptx) gene, a deleted or mutated dermonecrotic (dnt) gene, and a heterologous ampG gene. In some aspects, the *Bordetella* strain comprises a *Bordetella pertussis* strain. In other aspects, the wild-type *Bordetella* strain ampG gene is replaced by an *E.coli* ampG gene. In some aspects, the mutation of the ptx gene comprises the substitution of an amino acid involved in substrate binding and/or an amino acid involved in catalysis. In other aspects, the substitution of the amino acid involved in substrate binding comprises R9K and the substitution of the amino acid involved in catalysis comprises E129G. In some aspects, the *Bordetella* strain comprises a triple mutant strain.

In another aspect, the invention provides a vaccine comprising a composition of the invention for treating or preventing the influenza infection in the mammal. In some aspects, the vaccine comprises a *Bordetella* strain composition described herein. In some aspects, the vaccine is formulated for intranasal administration.

In another aspect, the invention provides a *Bordetella* strain identified by accession number CNCM I-3585.

In another aspect, the invention provides a *Bordetella* strain identified by accession number V09/009169.

BRIEF DESCRIPTION OF THE DRAWINGS

These and other features, aspects, and advantages of the invention will become better understood with regard to the following description, and accompanying drawings, where:

FIG. 5 shows viral load quantification in the lungs of protected versus non-protected mice. Adult Balb/c mice were nasally administered twice at a 4-week interval with $5 \times 10^6$ cfu of live BPZE1 bacteria and challenged 4 weeks later with a lethal dose (2LD50) of mouse-adapted H3N2 virus. Five animals per group were sacrificed 3 days post-viral challenge, their lungs were harvested and individually processed for in vitro determination of $TCID_{50}$ upon infection of MDCK cells. The viral load was compared with that obtained in non-treated mice. Results are representative of 3 independent experiments.

DETAILED DESCRIPTION

Introduction and Overview

Figure 1:
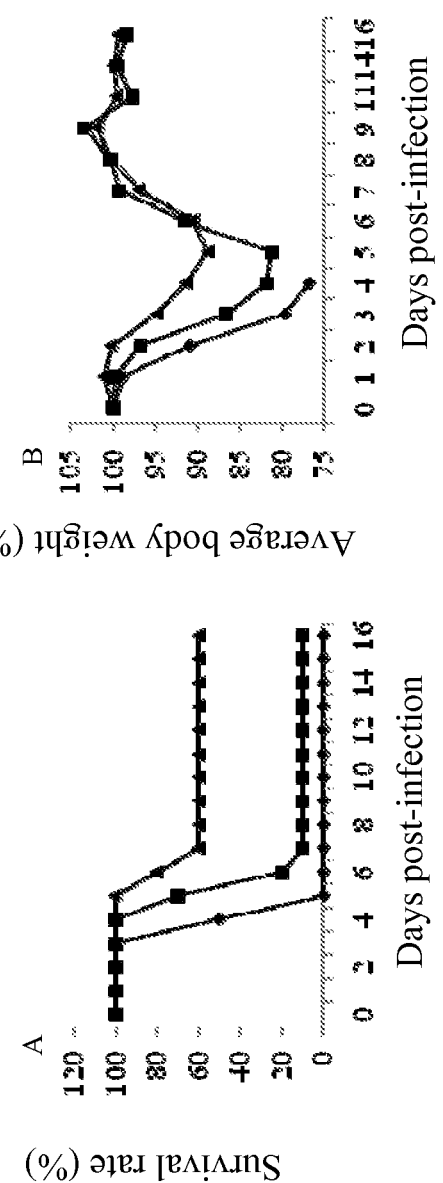
FIG. 1A-B shows protection rate of BPZE1-treated mice against lethal challenge with mouse-adapted H3N2 virus. Adult Balb/c mice were nasally administered with $5 \times 10^6$ cfu of BPZE1 bacteria and challenged either 3 weeks (solid square) or 6 weeks (solid triangle) later with a lethal dose (2LD50) of mouse-adapted H3N2 virus. Body weight changes were monitored daily and mice were euthanized when body weight loss exceeded 20% of the original body weight. Survival rates were compared to non-treated mice (solid lozenge). 10 animals per group were assessed. Results are representative of three independent experiments.

The invention relates to compositions and vaccines that include a mutated *Bordetella* strain for treating or preventing influenza infection in a mammal. In addition, the invention further provides methods for protecting a mammal against infection by influenza and/or eliciting an immune response against an influenza virus in a mammal using the composition or vaccine.

Terms used in the claims and specification are defined as set forth below unless otherwise specified.

As used herein, the abbreviation "PTX" refers to pertussis toxin, which synthesizes and secretes an ADP-ribosylating toxin. PTX is comprised of five different subunits (named S1-S5) with each complex containing two copies of S4. The subunits are arranged in an A-B structure. The A component is enzymatically active and is formed from the S1 subunit, while the B component is the receptor binding portion and is made up of subunits S2-S5.

As used herein the abbreviation "DNT" refers to pertussis dermonecrotic toxin, which is a heat labile toxin that can induce localized lesions in mice and other laboratory animals when it is injected intradermally.

As used herein the abbreviation "TCT" refers to tracheal cytotoxin, which is a virulence factor synthesized by *Bordetellae*. TCT is a peptidoglycan fragment and has the ability to induce interleukin-1 production and nitric oxide synthase. It has the ability to cause stasis of cilia and has lethal effects on respiratory epithelial cells.

The term "attenuated" refers to a weakened, less virulent *Bordetella* strain that is capable of stimulating an immune response and creating protective immunity, but does not generally cause illness.

The term "rapid protective immunity" means that immunity against *Bordetella* is conferred in a short time after administration of the mutated *Bordetella* strain of the invention.

The term "*Bordetella* strain" or "strain" includes strains from *Bordetella pertussis, Bordetella parapertussis*, and *Bordetella bronchiseptica*.

The term "child" is meant to be a person or a mammal between 0 months and 18 years of age.

"Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the invention to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods of the invention includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

"Concomitant administration" of a known drug (or other compound) with the composition of the invention means administration of the drug (or other compound) together with the composition at such time that both the known drug (or other compound) will have a therapeutic effect or diagnostic effect. Such concomitant administration can involve concurrent (i.e., at the same time), prior, or subsequent administration of the drug (or other compound) with respect to the administration of a composition of the invention. A person of ordinary skill in the art would have no difficulty determining the appropriate timing, sequence, and dosages of administration for particular drugs (or other compounds) together with compositions of the invention.

The terms "protection" and "prevention" are used herein interchangeably and mean that an infection by influenza is impeded.

"Prophylaxis vaccine" means that this vaccine prevents influenza infection upon future exposure.

The term "immunogenic composition" or "composition" means that the composition can induce an immune response and is therefore antigenic. By "immune response" means any reaction by the immune system. These reactions include the alteration in the activity of an organism's immune system in response to an antigen and can involve, for example, antibody production, induction of cell-mediated immunity, complement activation, or development of immunological tolerance.

As used herein, the term "disease" has the meaning generally known and understood in the art and comprises any abnormal condition in the function or well being of a host individual. A diagnosis of a particular disease by a healthcare professional can be made by direct examination and/or consideration of results of one or more diagnostic tests.

The terms "live vaccine composition", "live vaccine", "live bacterial vaccine", and similar terms refer to a composition comprising a strain of live *Bordetella* bacteria that provides at least partial protective immunity against influenza.

The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein.

The term "topical administration" refers to the application of a pharmaceutical agent to the external surface of the skin or the mucous membranes (including the surface membranes of the nose, lungs and mouth), such that the agent crosses the external surface of the skin or mucous membrane and enters the underlying tissues. Topical administration can result in a limited distribution of the agent to the skin and surrounding tissues or, when the agent is removed from the treatment area by the bloodstream, systemic distribution of the agent. In a preferred form, the agent is delivered by transdermal delivery, e.g., using a transdermal patch. Transdermal delivery refers to the diffusion of an agent across the skin (stratum comeum and epidermis), which acts as a barrier few agents are able to penetrate. In contrast, the dermis is permeable to absorption of many solutes and drugs, and topical administration therefor occurs more readily through skin which is abraded or otherwise stripped of the epidermis to expose the dermis. Absorption through intact skin can be enhanced by combining the active agent with an oily vehicle (e.g., creams, emollients, penetration enhancers, and the like, as described, e.g., in Remington's Pharmaceutical Sciences, current edition, Gennaro et al., eds.) prior to application to the skin (a process known as inunction).

The term "nasal administration" refers to any form of administration whereby an active ingredient is propelled or otherwise introduced into the nasal passages of a subject so that it contacts the respiratory epithelium of the nasal cavity, from which it is absorbed into the systemic circulation. Nasal administration can also involve contacting the olfactory epithelium, which is located at the top of the nasal cavity between the central nasal septum and the lateral wall of each main nasal passage. The region of the nasal cavity immediately surrounding the olfactory epithelium is free of airflow. Thus, specialized methods must typically be employed to achieve significant absorption across the olfactory epithelium.

The term "aerosol" is used in its conventional sense as referring to very fine liquid or solid particles carried by a propellant gas under pressure to a site of therapeutic application. A pharmaceutical aerosol of the invention contains a therapeutically active compound, which can be dissolved, suspended, or emulsified in a mixture of a fluid carrier and a propellant. The aerosol can be in the form of a solution, suspension, emulsion, powder, or semi-solid preparation. Aerosols of the invention are intended for administration as fine, solid particles or as liquid mists via the respiratory tract of a patient. Various types of propellants can be utilized including, but not limited to, hydrocarbons or other suitable gases. Aerosols of the invention can also be delivered with a nebulizer, which generates very fine liquid particles of substantially uniform size within a gas. Preferably, a liquid containing the active compound is dispersed as droplets, which can be carried by a current of air out of the nebulizer and into the respiratory tract of the patient.

The term "ameliorating" refers to any therapeutically beneficial result in the treatment of a disease state, e.g., an influenza-related disease state, including prophylaxis, lessening in the severity or progression, remission, or cure thereof In general, the phrase "well tolerated" refers to the absence of adverse changes in health status that occur as a result of the treatment and would affect treatment decisions.

"Synergistic interaction" refers to an interaction in which the combined effect of two or more agents is greater than the algebraic sum of their individual effects.

The term "in vitro" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process or method. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It is to be understood that this invention is not limited to particular methods, reagents, compounds, compositions, or biological systems, which can, of course, vary. It is also to be understood that the terminology used herein is for the purpose of describing particular aspects only, and is not intended to be limiting. As used in this specification and the appended claims, the singular forms "a", "an", and "the"

include plural referents unless the content clearly dictates otherwise. Thus, for example, reference to "a vaccine" includes a combination of two or more vaccines, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Influenza Virus Types

The invention is generally used to treat or prevent influenza virus infection in mammals. There are three types of influenza viruses that can be targeted by the invention: Influenza A, B, and C. Influenza type A viruses are divided into subtypes based on two proteins on the surface of the virus. These proteins are termed hemagglutinin (H) and neuraminidase (N). Influenza A viruses are divided into subtypes based on these two proteins. There are 16 different hemagglutinin subtypes H1, H2, H3, H5, H4, H6, H7, H8, H9, H10, H11, H12, H13, H14, H15 or H16 and 9 different neuraminidase subtypes N1, N2, N3, N4, N5, N6, N7, N8, or N9, all of which have been found among influenza A viruses in wild birds. Influenza A viruses include A(H1N1) and A(H3N2), both of which are examples of influenza viruses that can be targeted by the invention for treatment or prevention in a mammal. Diseases and symptoms typically caused by influenza virus infection can include: fever, coughing, sneezing, aches, fatigue, headache, watery eyes, nasal congestion, and abdominal pain. The invention can be used to treat or prevent these diseases.

Compositions

*Bordetella* Strains

The invention provides a mutated *Bordetella* strain that can be used as an immunogenic composition or a vaccine to elicit an immune response in a mammal. In one aspect, the mutated *Bordetella* strain contains a mutated ptx gene, a deleted or mutated dnt gene, and a heterologous ampG gene. The heterologous ampG gene product can reduce in large quantities the amount of tracheal cytotoxin that is produced. In one aspect, the strain is BPZE1. The starting strain which is mutated can be any *Bordetella* strain including *Bordetella pertussis, Bordetella parapertussis,* and *Bordetella bronchiseptica*. In one aspect the starting strain used to obtain the mutated *Bordetella* strain is *B. pertussis*. In another aspect, the strain is a triple mutant *Bordetella* strain. In another aspect, the *Bordetella* strain is identified by accession number CNCM 1-3585. In another aspect, the *Bordetella* strain is identified by accession number V09/009169.

The invention is not limited to only the mutants described above. Other additional mutations can be undertaken such as adenylate cyclase (AC) deficient mutants, lipopolysaccharide (LPS) deficient mutants, filamentous hemagglutinin (FHA), and any of the bvg-regulated components.

The construction of a mutated *Bordetella* strain of the invention can begin with replacing the *Bordetella* ampG gene in the strain with a heterologous ampG gene. Any heterologous ampG gene known in the art can be used in the invention. Examples of these can include all gram-negative bacteria that release very small amounts of peptidoglycan fragments into the medium per generation. Examples of gram-negative bacteria include, but are not limited to: *Escherichia coli, Salmonella, Enterobacteriaceae, Pseudomonas, Moraxella, Helicobacter, Stenotrophomonas, Legionella,* and the like. Typically, by replacing the *Bordetella* ampG gene with a heterologous ampG gene, the amount of tracheal cytotoxin (TCT) produced in the resulting strain expresses less than 1% residual TCT activity. In another aspect, the amount of TCT toxin expressed by the resulting strain is between about 0.6% to 1% residual TCT activity or about 0.4% to 3% residual TCT activity or about 0.3% to 5% residual TCT activity.

PTX is a major virulence factor responsible for the systemic effects of *B. pertussis* infections, as well as one of the major protective antigens. Due to its properties, the natural ptx gene can be replaced by a mutated version so that the enzymatically active moiety S1 codes for an enzymatically inactive toxin, but the immunogenic properties of the pertussis toxin are not affected. This can be accomplished by replacing the arginine (Arg) at position 9 of the sequence with a lysine (Lys) (R9K). Furthermore, a glutamic acid (Glu) at position 129 can be replaced with a glycine (Giy) (E129G). Generally these amino acid positions are involved in substrate binding and catalysis, respectively. In other aspects, other mutations can also be made such as those described in U.S. Pat. No. 6,713,072, incorporated herein by reference, as well as any known or other mutations able to reduce the toxin activity. In one aspect, allelic exchange can first be used to delete the ptx operon and then to insert a mutated version.

In another aspect of the invention, the dnt gene can be removed from the *Bordetella* strain using allelic exchange. Besides the total removal, the enzymatic activity can also be inhibited by a point mutation. Since DNT is constituted by a receptor-binding domain in the N-terminal region and a catalytic domain in the C-terminal part, a point mutation in the dnt gene to replace Cys-1305 to Ala-1305 inhibits the enzyme activity of DNT (Kashimoto T., Katahira J, Cornejo W R, Masuda M, Fukuoh A, Matsuzawa T, Ohnishi T, Horiguchi Y. (1999) Identification of functional domains of *Bordetella* dermonecrotizing toxin. *Infect. Immun.* 67: 3727-32.).

Besides allelic exchange to insert the mutated ptx gene and the inhibited or deleted dnt gene, the open reading frame of a gene can be interrupted by insertion of a genetic sequence or plasmid. This method is also contemplated in the invention. Other methods of generating mutant strains are generally well known in the art.

In one aspect of the invention, the mutated strain is called a BPZE1 strain and has been deposited with the Collection Nationale de Cultures de Microorganismes (CNCM) in Paris, France under the Budapest Treaty on Mar. 9, 2006 and assigned the number CNCM 1-3585. The mutations introduced into BPZE1 generally result in attenuation, but also allow the bacteria to colonize and persist. Thus, in another aspect, the invention provides BPZE1, which can induce mucosal immunity and systemic immunity when administered to a mammal in need thereof. In another aspect of the invention, a BPZE1 recombinant strain was constructed which expresses three copies of M2e peptide. This strain has been deposited with the National Measurement Institute (formerly AGAL) in Port Melbourne, Victoria, Australia 3207 under the Budapest Treaty on Apr. 27, 2009, and assigned the following accession number V09/009169. M2e is the extracellular portion of the M2 protein from influenza virus. It is highly conserved among all influenza A viruses and has been shown to induce an antibody-mediated protection against influenza A viruses. The recombinant M2e-producing BPZE1 strain can trigger (for example, upon nasal administration of the live bacteria) substantial anti-M2e antibody responses (local and systemic), allowing a significant protection against H1N1 and H3N2 challenge comparable to the BPZE1 bacteria alone.

The mutated *Bordetella* strains of the invention can be used in immunogenic compositions for the treatment or prevention of influenza virus infections. Such immunogenic compositions are useful to raise an immune response, either an antibody response and or a T cell response in mammals. For example, the T cell response can be such that it protects a mammal against influenza infection or against its consequences/diseases/symptoms.

The mutated *Bordetella* strains of the invention can be used as live strains in vaccines or immunogenic compositions. In one aspect, the live strains are used for nasal administration, while the chemically-or heat killed strains can be used for systemic or mucosal administration. In other aspects the stains are attenuated.

In other aspects of the invention, the strains do not include any heterologous genes other than the heterologous ampG gene described above. In yet other aspects, the strains do not include a heterologous expression platform (See, e.g., WO2007104451). Typically, heterologous expression platforms carry heterologous antigens. In one aspect, the heterologous expression platform can be used to deliver the heterologous antigens to the respiratory mucosa of a mammal.

Adjuvants

Compositions of the invention can be administered in conjunction with other immunoregulatory agents, including adjuvants. As used herein, the term "adjuvant" refers to a compound or mixture that enhances an immune response. In particular, compositions can include an adjuvant. Adjuvants for use with the invention can include, but are not limited to, one or more of the following set forth below:

Mineral Containing Adjuvant Compositions

Mineral containing compositions suitable for use as adjuvants in the invention include mineral salts, such as aluminum salts and calcium salts. The invention includes mineral salts such as hydroxides (e.g., oxyhydroxides), phosphates (e.g., hydroxyphosphates, orthophosphates), sulfates, and the like (e.g., see chapters 8 & 9 of Vaccine Design . . . (1995) eds. Powell & Newman. ISBN: 030644867X. Plenum.), or mixtures of different mineral compounds (e.g., a mixture of a phosphate and a hydroxide adjuvant, optionally with an excess of the phosphate), with the compounds taking any suitable form (e.g., gel, crystalline, amorphous, and the like), and with adsorption to the salt(s) being preferred. The mineral containing compositions can also be formulated as a particle of metal salt (WO/0023105).

Aluminum salts can be included in compositions of the invention such that the dose of $Al_3^+$ is between 0.2 and 1.0 mg per dose.

Oil-Emulsion Adjuvants

Oil-emulsion compositions suitable for use as adjuvants in the invention can include squalene-water emulsions, such as MF59 (5% Squalene,0.5% TWEEN 80, and 0.5% SPAN 85, formulated into submicron particles using a microfluidizer). See, e.g., WO90/14837. See also, Podda, "The adjuvanted influenza vaccines with novel adjuvants: experience with the MF59-adjuvanted vaccine", *Vaccine* 19: 2673-2680, 2001.

In other related aspects, adjuvants for use in the compositions are submicron oil-in-water emulsions. Examples of submicron oil-in-water emulsions for use herein include squalene/water emulsions optionally containing varying amounts of MTP-PE, such as a submicron oil-in-water emulsion containing 4-5% w/v squalene, 0.25-1.0% w/v TWEEN 80 (polyoxyelthylenesorbitan monooleate), and/or 0.25-1.0% SPAN 85 (sorbitan trioleate), and, optionally, N-acetylmuramyl-L-alanyl-D-isogluatminyl-L-alanine-2-(1'-2'-dipalmitoyl-s- n-glycero-3-huydroxyphosphoryloxy)-ethylamine (MTP-PE), for example, the submicron oil-in-water emulsion known as "MF59" (International Publication No. W090/14837; U.S. Pat. Nos. 6,299,884 and 6,451,325, incorporated herein by reference in their entirety; and Ott et al., "MF59--Design and Evaluation of a Safe and Potent Adjuvant for Human Vaccines" in Vaccine Design: The Subunit and Adjuvant Approach (Powell, M. F. and Newman, M. J. eds.) Plenum Press, New York, 1995, pp. 277-296). MF59 can contain 4-5% w/v Squalene (e.g., 4.3%), 0.25-0.5% w/v TWEEN 80, and 0.5% w/v SPAN 85 and optionally contains various amounts of MTP-PE, formulated into submicron particles using a microfluidizer such as Model 110Y microfluidizer (Microfluidics, Newton, MA). For example, MTP-PE can be present in an amount of about 0-500 μg/dose, or 0-250 μg/dose, or 0-100 μg/dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325, incorporated herein by reference in their entirety.

Complete Freund's adjuvant (CFA) and incomplete Freund's adjuvant (IFA) can also be used as adjuvants in the invention.

Saponin Adjuvant Formulations

Saponin formulations, can also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (*sarsaprilla*), Gypsophilla paniculata (brides veil), and *Saponaria officianalis* (soap root). Saponin adjuvant formulations can include purified formulations, such as QS21, as well as lipid formulations, such as Immunostimulating Complexes (ISCOMs; see below).

Saponin compositions have been purified using High Performance Thin Layer Chromatography (HPLC) and Reversed Phase High Performance Liquid Chromatography (RP-HPLC). Specific purified fractions using these techniques have been identified, including QS7, QS17, QS18, QS21, QH-A, QH-B and QH-C. A method of production of QS21 is disclosed in U.S. Pat. No. 5,057,540. Saponin formulations can also comprise a sterol, such as cholesterol (see WO96/33739).

Combinations of saponins and cholesterols can be used to form unique particles called ISCOMs. ISCOMs typically also include a phospholipid such as phosphatidylethanolamine or phosphatidylcholine. Any known saponin can be used in ISCOMs. For example, an ISCOM can include one or more of Quil A, QHA and QHC. ISCOMs are further described in EP0109942, WO96/11711, and WO96/33739. Optionally, the ISCOMS can be devoid of additional detergent. See WO00/07621.

A description of the development of saponin based adjuvants can be found at Barr, et al., "ISCOMs and other saponin based adjuvants", *Advanced Drug Delivery Reviews* 32: 247-27, 1998. See also Sjolander, et al., "Uptake and adjuvant activity of orally delivered saponin and ISCOM vaccines", *Advanced Drug Delivery Reviews* 32: 321-338, 1998.

Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins can be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, QB-phage (such as coat proteins), GA-phage, fr-phage, AP205 phage, and Ty (such as retrotransposon Ty protein p1).

Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3 dMPL). 3 dMPL is a mixture of 3 De-O-acylated monophosphoryl lipid A with 4, 5 or 6 acylated chains. An example of a "small particle" form of 3 De-O-acylated monophosphoryl lipid A is disclosed in EP 0 689 454. Such "small particles" of 3 dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g., RC-529. See Johnson et al., *Bioorg Med Chem Lett* 9: 2273-2278, 1999.

(2) Lipid A Derivatives

Lipid A derivatives can include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of Plasmodium berghei", *Vaccine* 21: 2485-2491, 2003; and Pajak, et al., "The Adjuvant OM-174 induces both the migration and maturation of murine dendritic cells in vivo", *Vaccine* 21: 836-842, 2003.

(3) Immunostimulatory Oligonucleotides

Immunostimulatory oligonucleotides suitable for use as adjuvants in the invention can include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine can be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", *Nucleic Acids Research* 31: 2393-2400, 2003; WO02/26757 and WO99/62923 for examples of analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence can be directed to Toll-like receptor (TLR9), such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence can be specific for inducing a Th1 immune response, such as a CpG-A ODN, or it can be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", *J. Immunol.* 170: 4061-4068, 2003; Krieg, "From A to Z on CpG", *TRENDS in Immunology* 23: 64-65, 2002, and WO01/95935.

In some aspects, the CpG oligonucleotide can be constructed so that the 5' end is accessible for receptor recognition. Optionally, two CpG oligonucleotide sequences can be attached at their 3' ends to form "immunomers". See, for example, Kandimalla, et al., "Secondary structures in CpG oligonucleotides affect immunostimulatory activity", *BBRC* 306: 948-95, 2003; Kandimalla, et al., "Toll-like receptor 9: modulation of recognition and cytokine induction by novel synthetic GpG DNAs", *Biochemical Society Transactions* 31: 664-658, 2003; Bhagat et al., "CpG penta- and hexadeoxyribonucleotides as potent immunomodulatory agents" *BBRC* 300: 853-861, 2003, and WO03/035836.

(4) ADP-Ribosylating Toxins and Detoxified Derivatives Thereof.

Bacterial ADP-ribosylating toxins and detoxified derivatives thereof can be used as adjuvants in the invention. For example, the toxin can be derived from *E. coli* (i.e., *E. coli* heat labile enterotoxin (LT)), cholera (CT), or pertussis (PTX). The use of detoxified ADP-ribosylating toxins as mucosal adjuvants is described in WO95/17211 and as parenteral adjuvants in WO98/42375. In some aspects, the adjuvant can be a detoxified LT mutant such as LT-K63, LT-R72, and LTR192G. The use of ADP-ribosylating toxins and detoxified derivaties thereof, particularly LT-K63 and LT-R72, as adjuvants can be found in the following references, each of which is specifically incorporated by reference herein in their entirety: Beignon, et al., "The LTR72 Mutant of Heat-Labile Enterotoxin of *Escherichia coli* Enahnces the Ability of Peptide Antigens to Elicit CD4+T Cells and Secrete Gamma Interferon after Coapplication onto Bare Skin", *Infection and Immunity* 70: 3012-3019, 2002; Pizza, et al., "Mucosal vaccines: non toxic derivatives of LT and CT as mucosal adjuvants", Vaccine 19: 2534-2541, 2001; Pizza, et al., "LTK63 and LTR72, two mucosal adjuvants ready for clinical trials" *Int. J. Med. Microbiol* 290: 455-461, 2003; Scharton-Kersten et al., "Transcutaneous Immunization with Bacterial ADP-Ribosylating Exotoxins, Subunits and Unrelated Adjuvants", *Infection and Immunity* 68: 5306-5313, 2000; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" *Infection and Immunity* 67: 6270-6280, 2003; Partidos et al., "Heat-labile enterotoxin of *Escherichia coli* and its site-directed mutant LTK63 enhance the proliferative and cytotoxic T-cell responses to intranasally co-immunized synthetic peptides", *Immunol. Lett.* 67: 09-216, 1999; Peppoloni et al., "Mutants of the *Escherichia coli* heat-labile enterotoxin as safe and strong adjuvants for intranasal delivery of vaccines", *Vaccines* 2: 285-293, 2003; and Pine et al., (2002) "Intranasal immunization with influenza vaccine and a detoxified mutant of heat labile enterotoxin from *Escheri-* chia coli (LTK63)" *J. Control Release* 85: 263-270, 2002. Numerical reference for amino acid substitutions is preferably based on the alignments of the A and B subunits of ADP-ribosylating toxins set forth in Domenighini et al., *Mol. Microbiol* 15: 1165-1167, 1995, specifically incorporated herein by reference in its entirety.

Bioadhesives and Mucoadhesives

Bioadhesives and mucoadhesives can also be used as adjuvants in the invention. Suitable bioadhesives can include esterified hyaluronic acid microspheres (Singh et al., *J. Cont. Rele.* 70 :267-276, 2001) or mucoadhesives such as cross-linked derivatives of poly(acrylic acid), polyvinyl alcohol, polyvinyl pyrollidone, polysaccharides and carboxymethylcellulose. Chitosan and derivatives thereof can also be used as adjuvants in the invention. See, for example, WO99/27960.

Adjuvant Microparticles

Microparticles can also be used as adjuvants in the invention. Microparticles (i.e., a particle of about 100 nm to about 150 μm in diameter, or 200 nm to about 30 μm in diameter, or about 500 nm to about 10 μm in diameter) formed from materials that are biodegradable and/or non-toxic (e.g., a poly(alpha-hydroxy acid), a polyhydroxybutyric acid, a polyorthoester, a polyanhydride, a polycaprolactone, and the like), with poly(lactide-co-glycolide) are envisioned, optionally treated to have a negatively-charged surface (e.g., with SDS) or a positively-charged surface (e.g., with a cationic detergent, such as CTAB).

Adjuvant Liposomes

Examples of liposome formulations suitable for use as adjuvants are described in U.S. Pat. No. 6,090,406, U.S. Pat. No. 5,916,588, and EP 0 626 169.

I. Polyoxyethylene Ether and Polyoxyethylene Ester Formulations

Adjuvants suitable for use in the invention can also include polyoxyethylene ethers and polyoxyethylene esters. WO99/52549. Such formulations can further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

In some aspects, polyoxyethylene ethers can include: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, or polyoxyethylene-23-lauryl ether.

Polyphosphazene (PCPP)

PCPP formulations for use as adjuvants are described, for example, in Andrianov et al., "Preparation of hydrogel microspheres by coacervation of aqueous polyphophazene solutions", *Biomaterials* 19: 109-115, 1998, and Payne et al., "Protein Release from Polyphosphazene Matrices", *Adv. Drug. Delivery Review* 31: 185-196, 1998.

Muramyl Peptides

Examples of muramyl peptides suitable for use as adjuvants in the invention can include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-s-n-glycero-3-ydroxyphosphoryloxy)-ethylamine MTP-PE).

Imidazoquinolone Compounds.

Examples of imidazoquinolone compounds suitable for use as adjuvants in the invention can include Imiquimod and its homologues, described further in Stanley, "Imiquimod and the imidazoquinolones: mechanism of action and therapeutic potential" *Clin Exp Dermatol* 27: 571-577, 2002 and Jones, "Resiquimod 3M", *Curr Opin Investig Drugs* 4: 214-218, 2003.

Human Immunomodulators

Human immunomodulators suitable for use as adjuvants in the invention can include cytokines, such as interleukins (e.g., IL-1, IL-2, IL-4, IL-5, IL-6, IL-7, IL-12, and the like), interferons (e.g., interferon-gamma), macrophage colony stimulating factor, and tumor necrosis factor.

Adjuvant Combinations

The invention can also comprise combinations of aspects of one or more of the adjuvants identified above. For example, adjuvant compositions can include:

(1) a saponin and an oil-in-water emulsion (WO99/11241);

(2) a saponin (e.g., QS21)+a non-toxic LPS derivative (e.g., 3 dMPL) (see WO94/00153);

(3) a saponin (e.g., QS21)+a non-toxic LPS derivative (e.g., 3 dMPL)+a cholesterol;

(4) a saponin (e.g., QS21)+3 dMPL+IL-12 (optionally+a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% TWEEN 80, 5% PLURONIC-block polymer L121, and thr-MDP, either microfluidized into a submicron emulsion or vortexed to generate a larger particle size emulsion.

(7) Ribi adjuvant system (RAS), (Ribi Immunochem) containing 2% Squalene, 0.2% TWEEN 80, and one or more bacterial cell wall components from the group consisting of monophosphorylipid A (MPL), trehalose dimycolate (TDM), and cell wall skeleton (CWS), preferably MPL +CWS (Detox); and (8) one or more mineral salts (such as an aluminum salt)+a non-toxic derivative of LPS (such as 3 dPML).

Aluminum salts and MF59 are examples of adjuvants for use with injectable influenza vaccines. Bacterial toxins and bioadhesives are examples of adjuvants for use with mucosally-delivered vaccines, such as nasal vaccines. All adjuvants noted above and others as generally known in the art to one of ordinary skill can be formulated for intranasal administration using techniques well known in the art.

Formulations and Carriers

Methods for treatment or prevention of diseases related to influenza virus infection (described in more detail below) are also encompassed by the invention. Said methods of the invention include administering a therapeutically effective amount of a composition of the invention. The composition of the invention can be formulated in pharmaceutical compositions. These compositions can comprise, in addition to one or more of the strains, a pharmaceutically acceptable excipient, carrier, buffer, stabilizer, or other materials well known to those skilled in the art. Such materials should typically be non-toxic and should not typically interfere with the efficacy of the active ingredient. The precise nature of the carrier or other material can depend on the route of administration, e.g., oral, intravenous, cutaneous or subcutaneous, nasal, intramuscular, or intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil, or synthetic oil. Physiological saline solution, dextrose, or other saccharide solution or glycols such as ethylene glycol, propylene glycol, or polyethylene glycol can be included.

For intravenous, cutaneous, or subcutaneous injection, or injection at the site of affliction, the active ingredient will be in the form of a parenterally acceptable aqueous solution which is pyrogen-free and has suitable pH, isotonicity, and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants, and/or other additives can be included, as required.

Administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of disease being treated. Prescription of treatment, e.g., decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in the latest edition of Remington's Pharmaceutical Science, Mack Publishing Company, Easton, Pa. ("Remington's").

Typically, a composition can be administered alone or in combination with other treatments, either simultaneously or sequentially dependent upon the condition to be treated.

Methods

Administration Routes

Compositions of the invention will generally be administered directly to a mammal. Direct delivery can be accomplished by parenteral injection (e.g., subcutaneously, intraperitoneally, intradermal, intravenously, intramuscularly, or to the interstitial space of a tissue), or mucosally, such as by rectal, oral (e.g., tablet, spray), vaginal, topical, transdermal (See e.g., WO99/27961) or transcutaneous (See e.g., WO02/074244 and WO02/064162), inhalation, intranasal (See e.g., WO03/028760), ocular, aural, pulmonary or other mucosal administration. Compositions can also be administered topically by direct transfer to the surface of the skin. Topical administration can be accomplished without utilizing any devices, or by contacting naked skin with the composition utilizing a bandage or a bandage-like device (see, e.g., U.S. Pat. No. 6,348,450).

In some aspects, the mode of administration is parenteral, mucosal, or a combination of mucosal and parenteral immunizations. In other aspects, the mode of administration is parenteral, mucosal, or a combination of mucosal and parenteral immunizations in a total of 1-2 vaccinations 1-3 weeks apart. In related aspects, the route of administration includes but is not limited to intranasal delivery.

Administration Procedures and Dosages

The invention can include administration of a mutated Bordetella strain to a mammal to elicit an immune response (e.g., a TH1 immune response) capable of impacting an influenza virus, e.g., H3N2. Examples of mutated Bordetella strains of the invention are described above. Typically, administration of the mutated Bordetella strain is used to treat or prevent an influenza virus infection in a mammal, e.g., a human, via protective immunity against the influenza virus. In some aspects, the mutated Bordetella strain administration is used to prevent influenza infection by administration prior to the influenza virus infection. Typically, the mutated Bordetella stain is administered to a mammal about less than 1, 1, 2, 3, 4, 5, 6, 7, 8, 9, 10, 11, 12, or more weeks prior to the influenza virus infection.

In one aspect, the method for treating or preventing an infection by an influenza virus includes administering to a subject in need thereof a single dose of a composition of the invention, e.g., BPZE1. In related aspects, the administering step is performed mucosally, e.g., intranasally.

In other aspects, composition of the invention is administered in more than one dose, e.g., two doses. The number of doses can vary as needed, for example the number of doses administered to a mammal can be 1, 2, 3, 4, 5, 6, 7, 8, 9, 10, or more doses. In one aspect, the method for treating or preventing an infection by an influenza virus, includes administering to a subject in need thereof a first immunogenic composition of the invention (comprising e.g., BPZE1) followed by a second immunogenic composition administration (comprising e.g., BPZE1). Typically, the time range between each dose of the composition can be about 1-6 days, or about 1, 2, 3, 4, 5, 6, 7, 8, 9, 10, 11, 12, 13, 14, 15, 20, 30, 40, 50, 60, 70, 80, 90, or more weeks. In related aspects, the time range between each dose is about 3 weeks. In other aspects, prime-boost-style methods can be employed where a composition of the invention can be delivered in a "priming" step and, subsequently, a composition of the invention is delivered in a "boosting" step.

The composition can typically be used to elicit systemic and/or mucosal immunity, for example to elicit an enhanced systemic and/or mucosal immunity. For example, the immune response can be characterized by the induction of a serum IgG and/or intestinal IgA immune response. Typically, the level of protection against influenza infection can be more than 50%, e.g., 60%, 70%, 80%, 90%, 91%, 92%, 93%, 94%, 95%, 96%, 97%, 98%, 99%, or more. In one aspect, the level of protection can be 100%. In other aspects the level of protection is less than 50%, e.g., 20%. In other aspects, the number of bacteria in each dosage is adjusted to attain an effective immune response in a mammal. The number of bacteria or cfus in each dosage can be about 1, 10, 100, 1000, 10000, 100000, 1000000, $5 \times 10^6$, or more or any dosage between said each dosage.

In other aspects the invention can also include co-administration of the composition with another agent or agents. Typically the various compositions/agents can be delivered in any order. Thus, in aspects including delivery of multiple different compositions or agents, the mutated Bordetella strain need not be all delivered before the agent, e.g., a drug, a siRNA, a miRNA, an immunogenic peptide, or a small molecule capable of effecting an influenza infection. Other examples of agents include neuraminidase inhibitors and M2 inhibitors (adamantanes). For example, the priming step can include delivery of one or more agents and the boosting can include delivery of one or more mutated Bordetella strains. In other aspects, multiple administrations of mutated Bordetella strains can be followed by multiple administrations of agents. Administrations can be performed in any order. Thus, one or more of the mutated Bordetella strains described herein and one or more agents can be co-administered in any order and via any administration route known in the art, e.g., to elicit an immune reaction.

In the invention, dosage treatment can be according to a single dose schedule or a multiple dose schedule. For example, multiple doses can be used in a primary immunization schedule and/or in a booster immunization schedule. In a multiple dose schedule, the various doses can be given by the same or different routes, e.g., a parenteral prime and mucosal boost, a mucosal prime and parenteral boost, and the like In other aspects, the dosage regime can enhance the avidity of the antibody response leading to antibodies with a neutralizing characteristic. An in-vitro neutralization assay can be used to test for neutralizing antibodies (see for example Asanaka et at , *J Virology* 102: 10327, 2005; Wobus et al., *PLOS Biology* 2; e432; and Dubekti et al., *J Medical Virology* 66: 400).

Tests to Determine the Efficacy or Presence of an Immune Response

One way of assessing efficacy of therapeutic treatment involves monitoring infection after administration of a composition of the invention. One way of assessing efficacy of prophylactic treatment involves monitoring immune responses against the antigens in the compositions of the invention after administration of the composition. Another way of assessing the immunogenicity of the compositions of the invention is to isolate the proteins or proteins mixes and to screen patient sera or mucosal secretions by immunoblot. A positive reaction between the protein and the patient serum indicates that the patient has previously mounted an immune response to the composition.

Another way of checking efficacy of therapeutic treatment involves monitoring infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the antigens in the compositions of the invention after administration of the composition. Typically, serum specific antibody responses are determined post-immunization but pre-challenge whereas mucosal specific antibody responses are determined post-immunization and post-challenge. The immunogenic compositions of the invention can be evaluated in vitro and in vivo animal models prior to host, e.g., human, administration.

The efficacy of compositions of the invention can also be determined in vivo by challenging animal models of infection, e.g., mice, with the compositions. The compositions can or can not be derived from the same strains as the challenge strains. In vivo efficacy models can include but are not limited to: (i) A murine infection model using human strains; (ii) a murine disease model which is a murine model using a mouse-adapted strain, such as strains which are particularly virulent in mice; and (iii) a primate model using human isolates.

The immune response induced by the invention can be one or both of a TH1 immune response and a TH2 response. The immune response can be an improved or an enhanced or an altered immune response. The immune response can be one or both of a systemic and a mucosal immune response. For example, the immune response can be an enhanced systemic and/or mucosal response. An enhanced systemic and/or mucosal immunity is reflected in an enhanced TH1 and/or TH2 immune response. For example, the enhanced immune response can include an increase in the production of IgG1 and/or IgG2a and/or IgA. In another aspect the mucosal immune response can be a TH2 immune response. For example, the mucosal immune response can include an increase in the production of IgA.

Typically, activated TH2 cells enhance antibody production and are therefore of value in responding to extracellular infections. Activated TH2 cells can typically secrete one or more of IL-4, IL-5, IL-6, and IL-10. A TH2 immune response can also result in the production of IgG1, IgE, IgA, and/or memory B cells for future protection. In general, a TH2 immune response can include one or more of an increase in one or more of the cytokines associated with a TH2 immune response (such as IL-4, IL-5, IL-6 and IL-10), or an increase in the production of IgG1, IgE, IgA and memory B cells. For example, an enhanced TH2 immune response can include an increase in IgG1 production.

A TH1 immune response can include one or more of an increase in CTLs, an increase in one or more of the cytokines associated with a TH1 immune response (such as IL-2, IFN-gamma, and TNF-alpha), an increase in activated macrophages, an increase in NK activity, or an increase in the production of IgG2a. For example, the enhanced TH1 immune response can include an increase in IgG2a production.

Compositions of the invention, in particular, an immunogenic composition comprising one or more strains of the invention can be used either alone or in combination with other agents optionally with an immunoregulatory agent capable of eliciting a Th1 and/or Th2 response.

The compositions of the invention can elicit both a cell-mediated immune response as well as a humoral immune response to effectively address an influenza infection. This immune response will preferably induce long lasting (e.g., neutralizing) antibodies and a cell-mediated immunity that can quickly respond upon exposure to one or more infectious antigens in the future.

Subjects and Mammals

Compositions of the invention are typically for preventing or treating influenza virus strains in mammalian subjects, e.g., humans. In some aspects, subjects can include the elderly (e.g., >65 years old), children (e.g., <5 years old), hospitalized patients, healthcare workers, armed service and military personnel, food handlers, pregnant women, the chronically ill, and people traveling abroad. The compositions are generally suitable for these groups as well as the general population or as otherwise deemed necessary by a physician.

Kits

The invention also provides kits comprising one or more containers of compositions of the invention. Compositions can be in liquid form or can be lyophilized. Suitable containers for the compositions include, for example, bottles, vials, syringes, and test tubes. Containers can be formed from a variety of materials, including glass or plastic. A container can have a sterile access port (for example, the container can be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device(s). The kit can further include a third component comprising an adjuvant.

The kit can also comprise a package insert containing written instructions for methods of inducing immunity, preventing infections, or for treating infections. The package insert can be an unapproved draft package insert or can be a package insert approved by the Food and Drug Administration (FDA) or other regulatory body.

The invention also provides a delivery device pre-filled with the compositions of the invention.

The pharmaceutical compositions are generally formulated as sterile, substantially isotonic and in full compliance with all Good Manufacturing Practice (GMP) regulations of the U.S. Food and Drug Administration.

From the foregoing description, various modifications and changes in the compositions and methods will occur to those skilled in the art. All such modifications coming within the scope of the appended claims are intended to be included therein. Each recited range includes all combinations and sub-combinations of ranges, as well as specific numerals contained therein.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

Exemplary Aspects

Below are examples of specific aspects for carrying out the invention. The examples are offered for illustrative purposes only, and are not intended to limit the scope of the invention in any way. Efforts have been made to ensure accuracy with respect to numbers used (e.g., amounts, temperatures, and the like), but some experimental error and deviation should, of course, be allowed for.

The practice of the invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's;* Carey and Sundberg *Advanced Organic Chemistry* $3^{rd}$ Ed. (Plenum Press) Volumes A and B, 1992).

Materials And Methods

Bacterial Strains and Growth Conditions

The bacterial strain used in this study is *B. pertussis* BPZE1, a streptomycin-resistant Tohamal derivative deleted for the dermonecortic (DNT)-encoding gene, producing inactivated pertussis toxin (PT) and background levels of tracheal cytotoxin (TCT) (22). BPZE1 bacteria were grown at 37° C. for 72 h on Bordet-Gengou (BG) agar (Difco, Detroit, Mich.) supplemented with 1% glycerol, 10% defibrinated sheep blood and 100 µg/ml streptomycin (Sigma Chemical CO., St Louis, Mo.). Liquid cultures were performed as described previously (Menozzi FD, et al., "Identification and purification of transferring- and lactoferrin-binding proteins of *Bordetella pertussis* and *Bordetella bronchiseptica*", *Infect. Immun* 59: 3982-3988, 1991) in Stainer-Scholte (SS) medium containing 1 g/l heptakis(2,6-di-o-methyl) β-cyclodextrin (Sigma). Heat-inactivation was performed at 95° C. for 1 hour.

Intranasal Infections. Six to eight week-old female Balb/c mice were kept under specific pathogen-free conditions in Individual Ventilated Cages, and all experiments were carried out under the guidelines of the National University of Singapore animal study board. For BPZE1 treatment, sedated mice were intranasally administered once, twice or three times (as indicated) with approximately 5×106 colony-forming units (cfu) of live or dead BPZE1 bacteria in 20 µl sterile PBS supplemented with 0.05% TWEEN 80 (Sigma) (PBST) as previously described (Mielcarek N, et al., "Intranasal priming with recombinant *Bordetella pertussis* for the induction of a systemic immune response against a heterologous antigen", *Infect immune* 65: 544-550, 1997). For influenza infection, sedated mice were nasally administered with approximately $2 \times 10^6$ TCID$_{50}$ of mouse-adapted A/Aichi/2/68 (H3N2) virus passage 10 (Narasaraju T, et al., "Adaptation of human influenza H3N2 virus in a mouse pneumonitis model: insights into viral virulence, tissue tropism and host pathogenesis", *Microbes Infect* 11: 2-11, 2009) or 4 lethal dose (LD)50 of H1N1(A/PR/8/34) influenza virus (ATCC# VR-95) in 20 µl sterile PBS supplemented with penicillin and streptomycin. Ten mice per group were used to determine the survival rates based on body weight loss and the mice were euthanized when body weight loss exceeded 20% of the original body weight.

Viral Titer Determination

Mouse lungs were harvested and homogenized using mechanical disruption (Omni homogenizer), and tested for the presence of viable virus by tissue culture infectious dose 50 (TCID$_{50}$) assay using a modified method reported by the WHO (WHO, "WHO Manual on Animals Influenza Diagnosis and Surveillance" (World Health Organization, Geneva), 2002). Briefly, 90% confluent Madin-Darby Canine Kidney (MDCK) cells in 96-well plates were inoculated with 100 µof 10-fold serially diluted lung homogenates. Plates were incubated at 35° C. in a humidified incubator (5% CO$_2$) for 3 days. TCID$_{50}$ was determined by a reduction in cytopathic effect (CPE) of 50%, and the log TCID$_{50}$/lung was derived. Five mice per group per time point were individually assessed.

Histopathologic Examination

Four mice per group were sacrificed and their lungs were harvested 3 days post-viral challenge. The lungs were removed and fixed in 10% formalin in PBS. After fixation, the lungs were embedded in paraffin, sectioned, and stained with H&E.

Cellular Infiltrates in Bronchoalveolar Lavage Fluids (BALFs)

Individual BALFs were recovered by injecting 1 ml of sterile PBS into the lungs of sacrificed animals and performing one lavage step ensuring that both lungs inflated during the process. BALFs were then centrifuged at 400 g for 10 min, and the supernatant was removed and stored at −80° C. for cytokine detection. Total BALF cell number was determined using a hemocytometer. The cells were spotted onto a glass slide using a Cytospin device (Thermo Shandon), and were stained with a modified Wright staining procedure (Kimman T G, et al., "Development and antigen specificity of the lymphoproliferation response of pigs to pseudorabies virus: dichotomy between secondary B- and T-cell responses", *Immunology* 86: 372-378, 1995). Identification of the different cell types was performed using standard morphological criteria. Results are expressed as the percentage of each cell type in the total cell population. A total of 500 cells were considered per slide. Four mice per group were individually assessed.

FACS Analysis.

Mice were sacrificed, their lungs were harvested and single cell suspensions were prepared by digesting the lungs at 37° C. for 15 min in 2 ml digestion buffer containing 0.5 mg/ml Liberase (Roche) in RPMI with 1% FCS and 2 U/ml DNaseI (Qiagen), followed by centrifugation on Ficoll-Paque™PLUS (GE) for 20 min at 600 g and room temperature. Cells were collected and washed twice with sterile FACS buffer (2% FCS, 5 mM EDTA in PBS). $10^6$ cells were stained with FITC-labeled anti-mouse CD3 antibody (eBioscience) and analyzed on CyAn™ ADP cytometer (Dako). Five mice per group per time point were individually assessed.

Cytokine and Chemokine Analysis

Cytokine and chemokine production in the BALFs supernatants was measured using Procarta cytokine profiling kit, according to the manufacturer's instructions (Panomics). After incubation with Ab-conjugated beads, detection Abs and streptavidin-PE complexes, samples were run on Bio-Plex instrument (Bio-Rad). Levels of the following growth factors, cytokines, and inflammatory mediators were evaluated: GM-CSF, KC, IL-1β, IL-6, IFN-γ and TNF-α, IFN-α, MCP-1 RANTES, IL-10. In addition, TGF-β levels were measured using a Human/Mouse TGFβ1 ELISA kit (eBioscience) according to the manufacturer's instructions.

Passive Transfer Experiment

A high titer anti-B. pertussis immune serum was generated in 10 adult Balb/c mice nasally infected twice at a 4-week interval with 5×10$^6$ cfu of live BPZE1 bacteria. Another group of 10 adult naïve Balb/c mice were injected intraperitoneally (ip.) with 10$^{5.5}$ TCID$_{50}$ of heat-inactivated human/Aichi/2/68 (H3N2) virus (HI-H3N2) in complete Freund's adjuvant and boosted with the same amount of HI-H3N2 virus in incomplete Freund's adjuvant 2 weeks later. The immune sera from each mouse group were collected 2 weeks after the boost, pooled and the anti-pertussis and anti-influenza antibody titers were measured by ELISA. Moreover, HI-H3N2 serum was tested for the presence of neutralizing antibodies by neutralization assay. The immune sera were filter-sterilized, heat inactivated at 56° C. for 30 min and stored at −80° C. until further use. Sera from control naïve mice were also collected as negative control.

Six to eight week-old recipient Balb/c mice were ip. injected with 200 μof naïve, anti-BPZE1 or anti-H3N2 immune serum 1 day prior viral challenge with mouse-adapted H3N2 virus. Body weight losses were monitored to determine the survival rates. Ten mice per group were assayed.

T Cell Proliferation Assay

Lymphocyte proliferation was measured by incorporation of tritiated ($^3$H) thymidine as described elsewhere (Bao Z, et al., "Glycogen synthase kinase-3beta inhibition attenuates asthma in mice", *Am J Respir Crit Care Med* 176: 431-438, 2007). Briefly, spleens from naïve and BPZE 1-treated mice (6 mice per group) were collected under aseptic condition and pooled. Single-cell suspensions were prepared and centrifuged on Ficoll-Paque™PLUS (GE) for 20 min at 600 g at room temperature. The isolated splenocytes were seeded in 96-well round-bottom plates (NUNC) at a density of 2×10$^5$ cells/well in 100 μl medium (RPMI640 supplemented with 10% FCS, 5×10−5 M β-mercaptoethanol, 2 mM L-glutamine, 10 mM HEPES, 200 U/ml penicillin, 200 μg/ml streptomycin). 100 μmedium containing 20 μg/ml of BPZE1 whole cell lysate or heat-inactivated 10$^5$ TCID$_{50}$ mouse-adapted H3N2 influenza virus (HI-H3N2) (test antigen) were added to the splenocytes. 100 ul of non-infected egg amniotic fluid and 100 ul of medium containing 5 μg/ml concanavalin A (conA) were used as mock and vitality controls, respectively. After 3 days of incubation at 37° C. in 5% CO2 atmosphere, the cultures were pulsed with 0.4 μCi [3H]thymidine in 20 μRPMI complete medium. After 18 hrs incubation, cells were harvested, washed and the incorporated radioactivity was measured in TopCount NXT™ Microplate Scintillation and Luminescence Counter (PerkinElmer). Results are expressed as stimulation index (SI) corresponding to the ratio between the mean of [$^3$H]thymidine uptake in the presence of test antigen and the mean of [$^3$H]thymidine uptake in the absence of test antigen. A SI>2 was considered positive. Each sample was assayed in quadruplicate.

IFN-α ELISPOT Assay

The frequency of antigen-specific IFN-γ-producing splenocytes was determined by ELISPOT assay using BD mouse ELISPOT set (BD PharMingen) according to the manufacturer's instructions. Briefly, single-cell suspensions of individual spleen from naïve and BPZE1-treated mice were prepared and plated in 96-well microplates (Millipore, Bedford, Mass.) pre-coated with 100 μof [5 μg/ml anti-IFN-γ antibody in sterile PBS] overnight at 4° C., washed three times and blocked for 2 hr at room temperature with RPMI 1640 containing 10% FCS. Cells were then incubated with 20 μg/ml of BPZE1 whole cell lysate or heat-inactivated 10$^5$ TCID$_{50}$ mouse-adapted H3N2 influenza virus (HI-H3N2) or 5 μg/ml conA for 12-20 hr at 37° C. in 5% CO$_2$ atmosphere. The plates were then washed followed by addition of biotin-conjugated anti-mouse IFN-γ antibody for 2 hr at room temperature. After washing, streptavidin-HRP conjugate was added and incubated at room temperature for 1 hr. Wells were washed again and developed with a 3-amino-9-ethyl-carbazole (AEC) substrate solution until spots were visible. After drying, spot-forming cell numbers were counted by Bioreader® 4000 (Biosystem). Six animals per group were individually assayed.

Statistical Analysis

Unless otherwise stated, bars represent means±SD and averages were compared using a bidirectional unpaired Student's t test with a 5% significance level with * p≤0.05, p≤0.01 and *p≤0.001.

EXAMPLE 1

Figure 2:
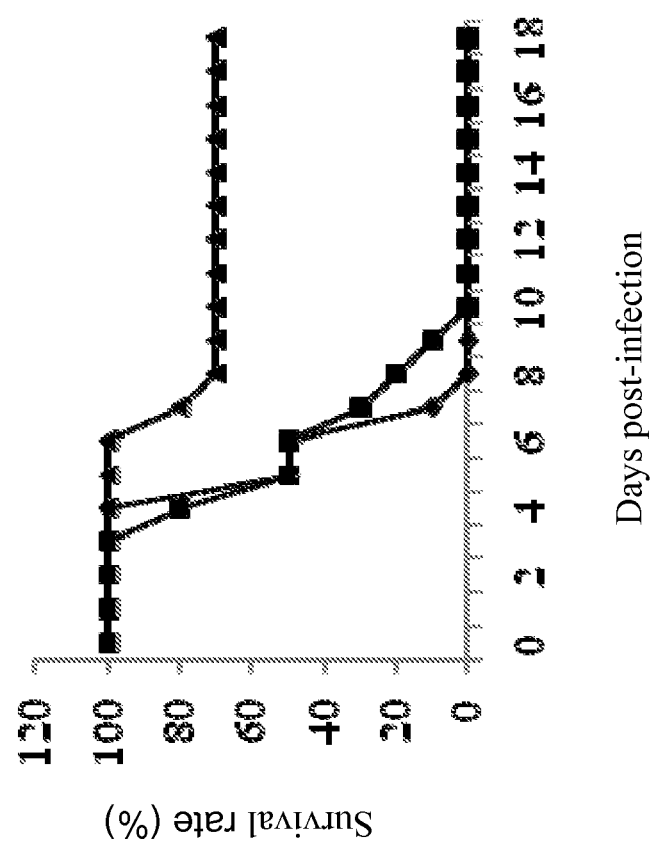
FIG. 2 shows protection rates against lethal challenge with mouse-adapted H3N2 virus in mice treated with dead versus live BPZE1 bacteria. Adult Balb/c mice were nasally administered with $5 \times 10^6$ cfu of live (solid triangle) or dead (solid square) BPZE1 bacteria, and challenged 6 weeks later with a lethal dose (2LD50) of mouse-adapted H3N2 virus. Body weight changes were monitored daily and mice were euthanized when body weight loss exceeded 20% of the original body weight. Survival rates were compared to non-treated mice (solid lozenge). 10 animals per group were assessed. Results are representative of two independent experiments.

A Single Nasal Administration of Live Attenuated *Bordetella Pertussis* Protects Against H3n2 Influenza Challenge A mouse-adapted H3N2 influenza virus was obtained through successive lung-to-lung passages of the A/Aichi/2/68 (H3N2) virus into adult Balb/c mice (Narasaraju T, et al., "Adaptation of human influenza H3N2 virus in a mouse pneumonitis model: insights into viral virulence, tissue tropism and host pathogenesis", *Microbes Infect* 11: 2-11, 2009). Passage 10 (P10) strain exhibited high virulence, causing extra-pulmonary spread with necrotic and inflammatory lesions in the various organs of the infected animals. Nasal administration of $2\times10^6$ $TCID_{50}$ of the P10 viral suspension caused the death of the animals within 4 days (Narasaraju T, et al., "Adaptation of human influenza H3N2 virus in a mouse pneumonitis model: insights into viral virulence, tissue tropism and host pathogenesis", *Microbes Infect* 11:2-11, 2009).

Adult Balb/c mice were nasally inoculated with live BPZE1 bacteria and subsequently challenged either 3 or 6 weeks later with a lethal dose of mouse-adapted H3N2 virus. Survival rate based on body weight changes indicated that the mice challenged 3 weeks after nasal BPZE1 treatment were not significantly protected whereas 60% protection was achieved when mice were challenged 6 weeks post-BPZE1 treatment (FIG. 1).

EXAMPLE 2

Live But Not Dead Bpze1 Bacteria Protect Against Lethal H3n2 Challenge

Adult Balb/c mice were nasally administered once with live or dead BPZE1 bacteria and were subsequently challenged with a lethal dose of mouse-adapted H3N2 virus 6 weeks post-BPZE1 treatment. The results showed that dead bacteria did not provide any significant protection against H3N2 (FIG. 2), suggesting that bacterial colonization of the mouse lung is necessary to induce the protective mechanisms.

EXAMPLE 3

Boost Effect

Figure 3:
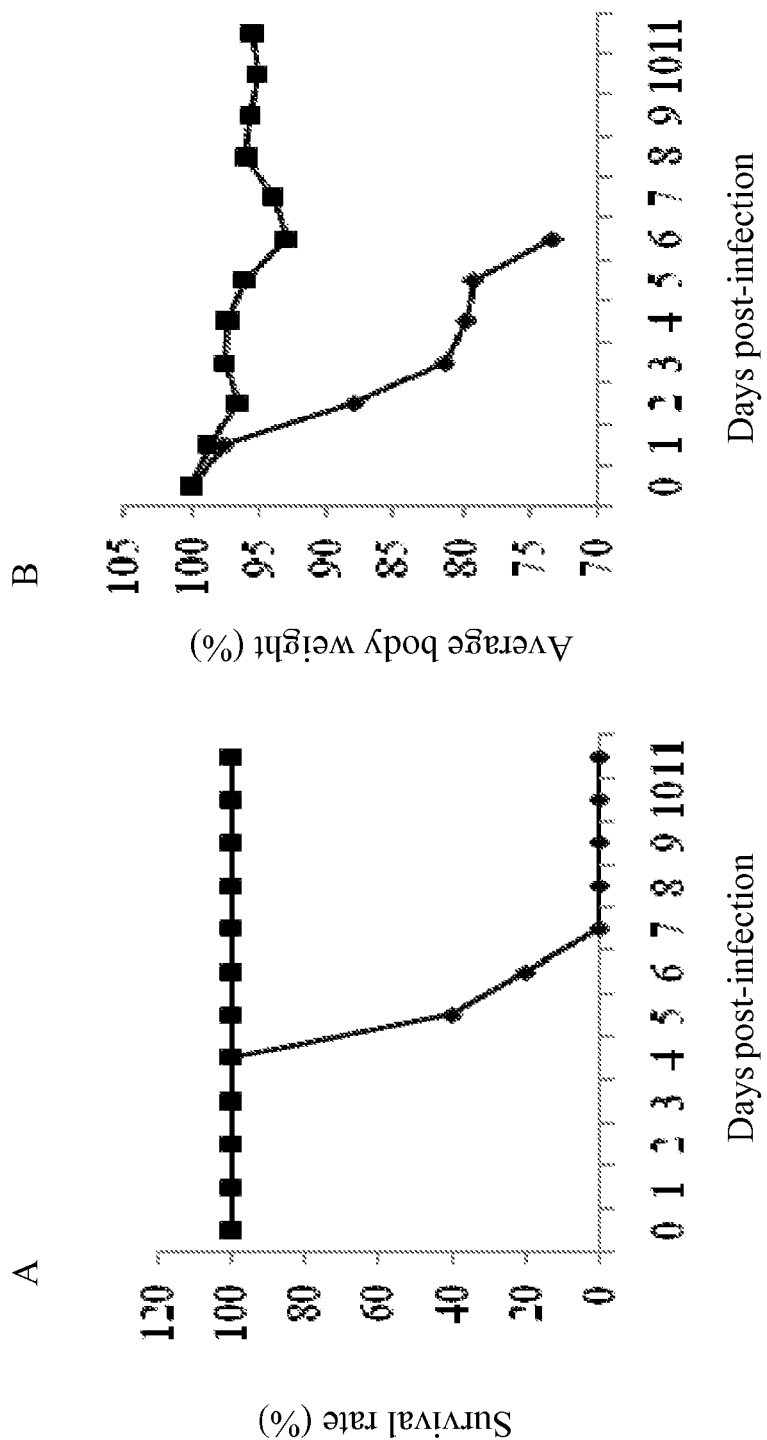
FIG. 3 A-B shows protection rate against lethal challenge with mouse-adapted H3N2 virus in mice treated twice with live BPZE1 bacteria. Adult Balb/c mice were nasally administered twice at a 4-week interval with $5 \times 10^6$ cfu of BPZE1bacteria (solid square) and challenged 4 weeks later with a lethal dose (2LD50) of mouse-adapted H3N2 virus. Body weight changes were monitored daily and mice were euthanized when body weight loss exceeded 20% of the original body weight. Survival rates were compared to non-treated mice (solid lozenge). 10 animals per group were assessed. Results are representative of two independent experiments.

Live BPZE1 bacteria were nasally administered to Balb/c mice twice at a 4-week interval prior lethal challenge with mouse-adapted H3N2 virus performed 4 weeks after the last BPZE1 administration. A 100% protection rate was obtained for the BPZE1-treated animals with minimal body weight changes (FIG. 3). Similar protection rate was achieved when the viral challenge was performed 2 weeks after the boost. These data indicated that a second nasal administration of live BPZE1 bacteria not only enhanced the protection efficacy but also shortened the time necessary to trigger the protective mechanisms.

EXAMPLE 4

Bpze1 Bacteria Provide Protection Against H1n1 Virus Challenge

Figure 4:
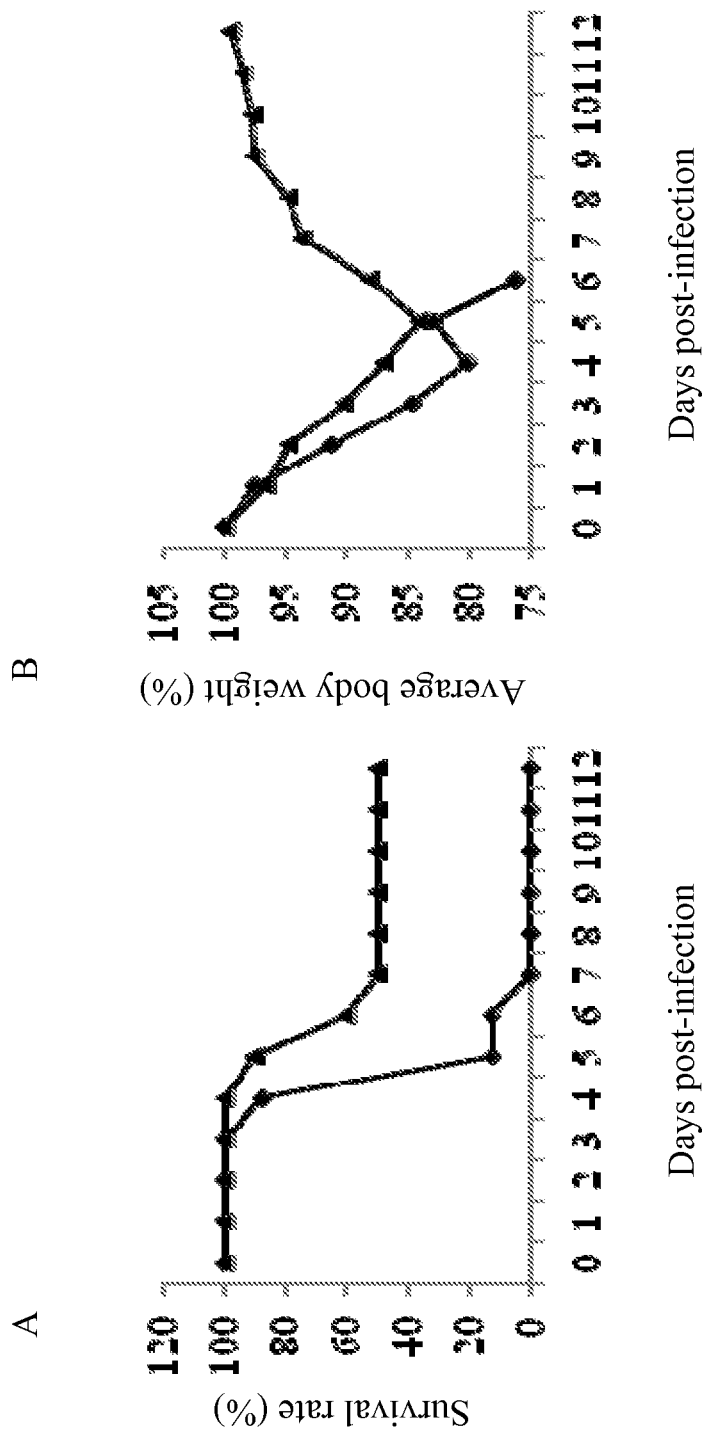
FIG. 4 A-B protection rate of BPZE1-treated mice against lethal challenge with H1N1 influenza A virus. Adult Balb/c mice were nasally administered three times at 4-week and 3-week intervals (solid triangle) with $5 \times 10^6$ cfu of live BPZE1 bacteria. The animals were challenged with a lethal dose (4 LD50) of A/PR/8/34 (H1N1) influenza A virus 2 weeks after the last BPZE1 treatment. Body weight changes were monitored daily and mice were euthanized when body weight loss exceeded 20% of the original body weight. Survival rates were compared to non-treated mice (solid lozenge). 10 animals per group were assessed. Resulst are representative of 2 independent experiments.

The protective potential of BPZE1 bacteria against influenza A viruses was further explored. Mice nasally treated once with live BPZE1 bacteria were not protected against a lethal challenge with human A/PR/8/34 (H1N1) influenza A virus performed 6 weeks later (data not shown). However, three consecutive administrations of live BPZE1 bacteria conferred 50% protection against H1N1 virus (FIG. 4). These observations indicated that BPZE1 bacteria can have the potential to protect against all influenza A viruses although with a variable efficacy.

EXAMPLE 5

The Viral Load is Not Reduced in the Protected Mice

Figure 5:
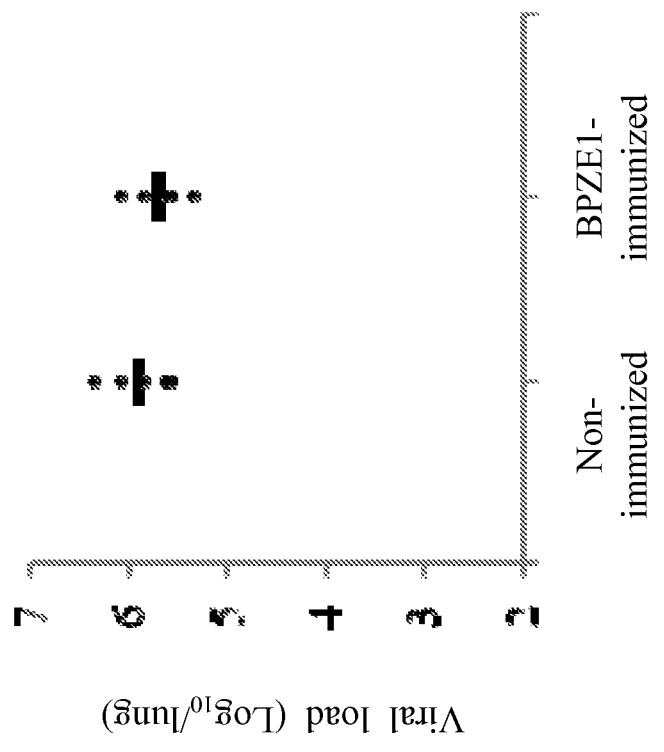

To further characterize the cross-protection against influenza A viruses, the viral load was quantified in the lungs of mice treated twice with BPZE1 bacteria and in control mice. The virus load was checked 3 days post-infection which corresponds to the peak of virus titer in mice infected with mouse-adapted H3N2 virus (Narasaraju T, et al., "Adaptation of human influenza H3N2 virus in a mouse pneumonitis model: insights into viral virulence, tissue tropism and host pathogenesis", *Microbes Infect* 11: 2-11, 2009). No significant difference in the viral load was observed between the two animal groups (FIG. 5). This result suggested that the cross-protective mechanisms triggered in the BPZE1-treated animals do not directly target the virus particles and/or infected cells.

EXAMPLE 6

Bpze1 Treatment Protects Mice from Influenza-Induced Immunopathology and Lymphocyte Depletion Lung immunopathology was examined by histology of lung sections from infected BPZE1-treated animals and control mice. As expected and as described previously (Narasaraju T, et al., "Adaptation of human influenza H3N2 virus in a mouse pneumonitis model: insights into viral virulence, tissue tropism and host pathogenesis", *Microbes Infect* 11: 2-11, 2009), the infected control mice displayed severe inflammation with inflammatory cells, severe bronchopneumonia and interstitial pneumonitis with bronchioles and alveoli filled with necrotic debris as well as high pulmonary emphysema and moderate edema (FIG. 7A). In contrast, only mild inflammation, minimal airway and alveolar damage, and mild perivascular/peribronchular damage associated with minimal edema were observed in the lungs of the protected BPZE1-treated mice.

Figure 6:
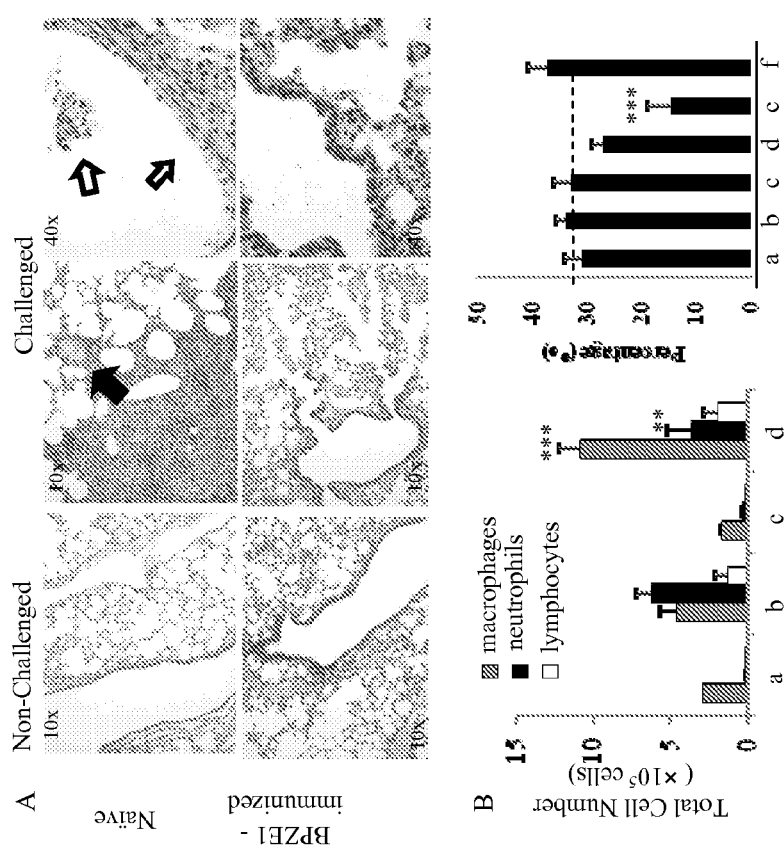
FIG. 6 A-B shows lung histology and cellular infiltrates and $CD3^+$ T cell population in the lungs in BPZE1-treated versus non-treated mice after lethal viral challenge. Adult Balb/c mice were nasally administered with $5 \times 10^6$ cfu of live BPZE1 bacteria and challenged 6 weeks later with a lethal dose (2LD50) of mouse-adapted H3N2 virus. Three days post-viral challenge, mice were euthanized and their lungs were individually processed for histology analysis (A) or broncho-alveolar lavages for analysis of the cellular infiltrates (B). Legend A: Infected control mice displayed severe inflammation, pulmonary edema (black arrow) and severe necrotizing bronchitis with necrotic cell debris (open arrow). Infected BPZE1-treated mice showed only minimal inflammation and airway damage, and mild peribronchular damage. Representative fields are shown. Results were equivalent in more than 40 fields analyzed per group (>5 fields/section, 2 sections/mouse and 4 mice/group). Legend B: a, naïve mice non-challenged; b, naïve mice challenged with H3N2 virus; c, BPZE1-treated mice non-challenged; d, BPZE1-treated mice challenged with H3N2 virus. Four animals per time point per group were individually assessed. , $p \leq 0.01$; *, $p \leq 0.001$. Results are representative of two independent experiments. (C). FACS analysis of the CD3+ T cell population in the mice lungs. 3 days or 5 days after lethal H3N2 influenza virus challenge, non-treated control mice and mice treated twice with BPZE1 were euthanized and $CD3^+$ T cell population in their lungs were analyzed by flow cytometry. Four animals per time point per group were individually assessed. Results are expressed in percentage of CD3' T cells in the total lung cell population. mean±SD. Legend: a, naïve mice non-challenged; b, BPZE1-treated mice non-challenged; c, naïve mice challenged with H3N2 virus and sacrificed 3 days later; d, BPZE1-treated mice challenged with H3N2 virus and sacrificed 3 days later; e, naïve mice challenged with H3N2 virus and sacrificed 5 days later; f, BPZE1-treated mice challenged with H3N2 virus and sacrificed 5 days later. ***, p<0.001.

The cell populations present in the broncho-alveolar lavage fluids (BALFs) recovered from protected and non-protected animals were also examined. Whereas the total number of cells present in the BALFs from both animal groups were comparable ($11.8 \times 10^5$ versus $16.1 \times 10^5$), a significantly higher number of macrophages and lower number of neutrophils were found in the BPZE1-treated mice (FIG. 6B).

Furthermore, the lymphocyte population present in the lungs of protected and non-protected mice was analysed. Lymphocyte depletion has indeed been reported in mice infected with highly pathogenic H1N1(1918) and H5N1 influenza viruses (Kash J C, et al., "Genomic analysis of increased host immune and cell death responses induced by 1918 influenza virus", *Nature* 443: 578-581, 2006; Uiprasertkul M, et al., "Apoptosis and Pathogenesis of Avian Influenza A (H5N1) Virus in Humans", *Emerg Infect Dis* 13: 708-712, 2007; Lu X, et al., "A mouse model for the evaluation of pathogenesis and immunity to influenza A (H5N1) viruses isolated from humans", *J Virol* 73: 5903-5911, 1999) as well as in mice infected with the mouse-adapted H3N2 virus strain used in this work (Narasaraju T, et al., "Adaptation of human influenza H3N2 virus in a mouse pneumonitis model: insights into viral virulence, tissue tropism and host pathogenesis", *Microbes Infect* 11: 2-11, 2009). Here, Balb/c mice were treated twice with BPZE1 bacteria and challenged with mouse-adapted H3N2 virus 4 weeks later. The mouse lungs were harvested 3 and 5 days post-influenza challenge for FACS analysis of the T cell population. Three days post-viral challenge, the percentage of $CD3^+$ T lymphocytes in the infected control mice and BPZE1-treated mice was comparable to the percentage found in the animals before challenge (FIG. 6C). However, a significant $CD3^+$ T cell depletion was observed in the infected control animals 5 days post-viral challenge (FIG. 6C) as reported before (Narasaraju T, et al., "Adaptation of human influenza H3N2 virus in a mouse pneumonitis model: insights into viral virulence, tissue tropism and host pathogenesis", *Microbes Infect* 11: 2-11, 2009). In contrast, the T cell population remained constant before and after challenge in the protected BPZE1-immunized animals (FIG. 6C), suggesting that BPZE 1-treatment prevented influenza-induced lymphocyte depletion.

EXAMPLE 7

Figure 7:
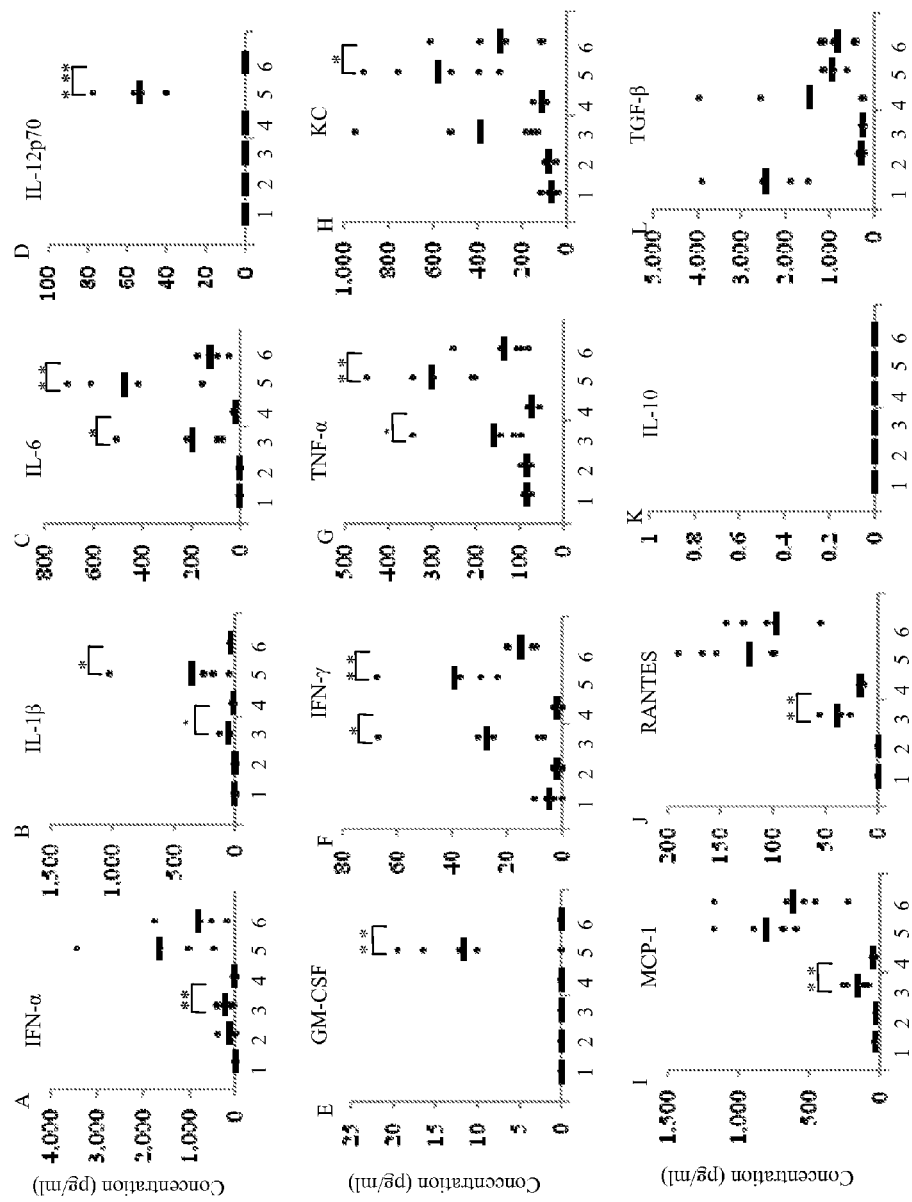
FIG. 7 A-L shows pro- and anti-inflammatory cytokine and chemokine profiles in the BPZE1-treated versus non-treated mice after lethal H3N2 viral challenge. Adult Balb/c mice were nasally administered twice at a 4-week interval with 5×10$^6$ cfu of live BPZE1 bacteria and were challenged with a lethal dose (2LD50) of mouse-adapted H3N2 virus 4 weeks after the last administration. One and three days post-viral challenge, five mice per group and per time point were sacrificed and broncho-alveolar lavages fuilds (BALFs) were collected. 14 inflammation-related cytokines and chemokines were measured in each individual BALF sample. Legend: 1, non-treated non-challenged mice; 2, BPZE 1-treated non-challenged mice; 3, non-treated challenged mice and sacrificed 1 day post-challenge; 4, BPZE 1-treated challenged mice and sacrificed 1day post-challenge; 5, non-treated challenged mice and sacrificed 3 days post- challenge; 6, BPZE1-treated challenged mice and sacrificed 3 days post-challenge. *, p<0.05; , p<0.01; *, p<0.001.

The Production of Pro-Inflammatory Cytokines and Chemokines is Dampened in the Protected Bpze1-Treated Mice Major pro-inflammatory cytokines and chemokines were measured in the BALFs recovered from protected BPZE1-treated mice and compared to non-protected mice, 1 and 3 days after lethal H3N2 virus challenge. All the pro-inflammatory cytokines and chemokines measured in the BALFs of the protected animal group were significantly lower than those measured in the non-protected mice (FIG. 7). The differences were observed at both day 1 and day 3 for IL-1β, IL-6, IFN-γ and TNF-α, which are the main pro-inflammatory cytokines contributing to influenza-induced immunopathology and correlating with disease severity (de Jong M D, et al., "Fatal outcome of human influenza A (H5N1) is associated with high viral load and hypercytokinemia", *Nat Med* 12: 1203-1207, 2006; Beigel J H, et al., "Avian influenza A (H5N1) infection in humans:, *N Engl J Med* 353: 1374-1385, 2005; Peiris J S, et al., "Re-emergence of fatal human influenza A subtype H5N1 disease", *Lancet* 363: 617-619, 2004; Schmitz N, et al., "Interleukin-1 is responsible for acute lung immunopatholoy but increases survival of respiratory influenza virus infection", *J Virol* 79: 6441-6448, 2005). The levels of IFN-α, MCP-1 and RANTES were found significantly reduced 1 day post-viral challenge whereas the production of IL-12 (p70), GM-CSF and KC was lower at day 3 post-challenge. Strikingly, complete suppression of IL-12 production was found in the protected animal group, consistent with lower levels of IFN-γ.

Furthermore, no significant difference was detected in the levels of anti-inflammatory cytokines IL-10 and TGF-β between protected and non-protected animals, ruling out the involvement of type 1 regulatory T cells (Tr1) in the cross-protection mechanisms (FIG. 7).

EXAMPLE 8

Figure 8:
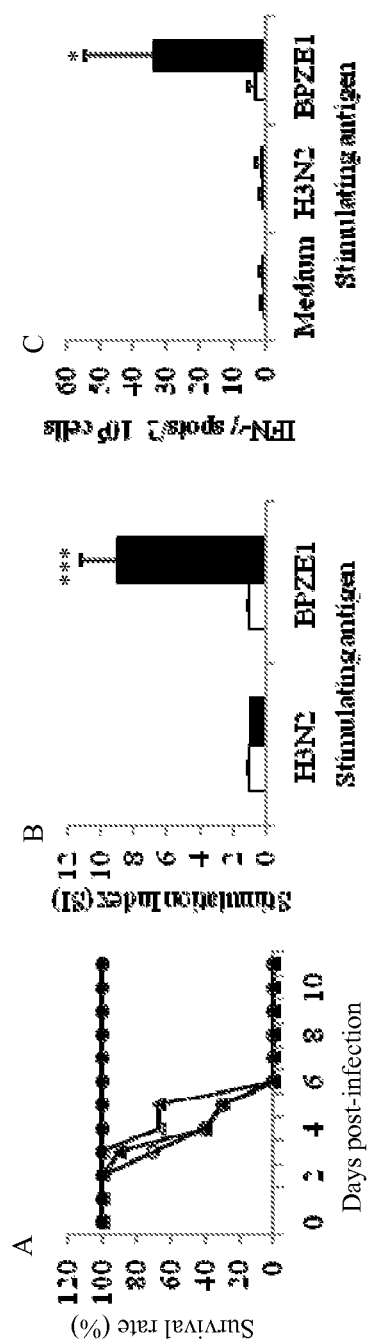
FIG. 8 A-C shows role of the *B. pertussis*-specific immunity in the cross-protection. (A). Naive (open triangle) or anti-H3N2 (solid circle) or anti-BPZE1 (open circle) immune serum was ip. injected to adult naïve Balb/c mice one day prior to lethal challenge (2LD50) with mouse-adapted H3N2 virus. Body weight changes were monitored daily and mice were euthanized when body weight loss exceeded 20% of the original body weight. Survival rates were compared to non-treated mice (solid triangle). 10 animals per group were assessed. (B) & (C). Adult Balb/c mice were nasally administered with 5×10$^6$ cfu of live BPZE1 bacteria and 6 weeks later the animals were euthanized and their spleens were harvested. Pooled (B) or individual (C) splenocytes from 6 animals were stimulated with either BPZE1 lysate or heat-inactivated H3N2 virus particles. $^3$H-thymidine incorporation (B) and IFN-γ ELISPOT assay (C) were performed as described below. Representative of two different experiments, both showed similar results; mean±SD; *, p<0.05, ***, p<0.001.

*B. Pertussis*-Specific Adaptive Immunity is not Involved in the Cross-Protection The presence of cross-reactive (and protective) antibodies and/or T cells in the BPZE1-treated animals was examined. Firstly, a BLAST search failed to identify any matching epitopes between *B. pertussis* and influenza A H3N2 and H1N1 viruses (data not shown). Secondly, the immune serum from BPZE 1-treated mice did not react with whole H3N2 viral particles in an ELISA assay, neither did it neutralize the virus in an in vitro neutralization assay (data not shown). Thirdly, a high-titer anti-BPZE1 immune serum did not confer any protection against H3N2 lethal challenge in an in vivo passive transfer experiment whereas an immune serum raised against heat-inactivated H3N2 virus gave a 100% protection rate (FIG. 8A). Fourthly, proliferation and IFN-γ ELISPOT assays showed that splenocytes from BPZE1-treated mice did not proliferate and did not produce IFN-γ respectively upon stimulation with H3N2 viral particles (FIGS. 8B & C). Altogether, these data strongly support that *B. pertussis*-specific immunity does not play any role in the cross-protection against influenza A viruses.

Discussion

Severe respiratory disease and immunopathology together with a high case-fatality rate have become a hallmark of highly pathogenic avian influenza virus infection in humans as well as in other mammalian species. However, the underlying mechanisms accounting for the severe immunopathological effects have yet to be fully elucidated. In particular, relationship between viral load, immunopathology and disease outcome remains elusive. Several previous studies have reported a reduced mortality rate and immunopathology without significant reduction of the viral burden in animal models of influenza infection; For example, reduced inflammatory cell infiltration and pulmonary damage but with delayed viral clearance was observed in mice with disrupted MIP-1α gene (Cook DN, et al., "Requirement of MIP-1 alpha for an inflammatory response to viral infection", *Science* 269: 1583-1585, 1995). Likewise, CCR2 (primary receptor for MCP-1)-deficient mice displayed reduced mortality but a significantly elevated viral burden associated with decreased pulmonary cell infiltration and tissue damage (Dawson T C, et al., "Contrasting effects of CCR5 and CCR2 deficiency in the pulmonary inflammatory response to influenza A virus", *Am J Pathol* 156: 1951-1959, 2000). In contrast, IL-1R knock-out mice showed increased mortality associated with delayed viral clearance but less severe pathology (Schmitz N, et al., "Interleukin-1 is responsible for acute lung immunopatholoy but increases survival of respiratory influenza virus infection", *J Virol* 79: 6441-6448, 2005).

Here, we report that *B. pertussis*-mediated cross-protection against influenza A viruses does not result a in lower virus load in the lungs. Instead, protected BPZE1-treated mice displayed minimal lung immunopathology and reduced production of the major pro-inflammatory cytokines and chemokines Our finding is in agreement with the general consensus that disease severity correlates strongly with high cytokines/chemokines levels (La Gruta N L, et al., "A question of self-preservation: immunopathology in influenza virus infection", *Immunol Cell Biol* 85: 85-92 2007). Cytokine storm, characterized by excessive levels of chemokines and cytokines in the serum and lungs due to uncontrolled activation of the host's immune system, was indeed correlated with the fatal outcome of experimental animals infected with reconstructed 1918 H1N1 and H5N1 influenza viruses (Kash J C, et al., "Genomic analysis of increased host immune and cell death responses induced by 1918 influenza virus", *Nature* 443: 578-581, 2006; Simon A K, et al., "Tumor necrosis factor-related apoptosis-inducing ligand in T cell development: sensitivity of human thymocytes", *Proc Natl Acad Sci USA* 98: 5158-5163, 2001; Kobasa D, et al., "Aberrant innate immune response in lethal infection of macaques with the 1918 influenza virus", *Nature* 445: 319-323, 2007; Tumpey T M, et al., "Characterization of the reconstructed 1918 Spanish influenza pandemic virus", *Science* 310: 77-80, 2005) as well as in humans (de Jong M D, et al., "Fatal outcome of human influenza A (H5N1) is associated with high viral load and hypercytokinemia", *Nat Med* 12: 1203-1207, 2006; Beigel J H, et al., "Avian influenza A (H5N1) infection in humans:, *N Engl J Med* 353: 1374-1385, 2005; Uiprasertkul M, et al., "Apoptosis and Pathogenesis of Avian Influenza A (H5N1) Virus in Humans", *Emerg Infect Dis* 13: 708-712, 2007; Peiris J S, et al., "Re-emergence of fatal human influenza A subtype H5N1 disease", *Lancet* 363: 617-619, 2004). Furthermore, histological and pathological indicators strongly suggest a key role for an excessive host response in mediating at least some of the extreme pathology associated with highly pathogenic influenza viruses. However, the role of each individual cytokine during influenza infection has remained unclear with often both positive and negative effects; Although their production can be important for viral clearance through the recruitment and/or activation of immune effector cells on the site of infection, their inflammatory properties can also lead to tissue damage (La Gruta N L, et al., "A question of self-preservation: immunopathology in influenza virus infection", *Immunol Cell Biol* 85: 85-92 2007).

The reduced production of pro-inflammatory cytokines and chemokines in the respiratory tract of the protected BPZE 1-treated animals likely impacted on cellular infiltration and immune cell activation; A significantly lower neutrophil counts was indeed observed in the BALFs of the protected animals consistent with lower levels of KC and TNF-α, both cytokines being involved in the recruitment and activation of neutrophils in the infected tissues (La Gruta N L, et al., "A question of self-preservation: immunopathology in influenza virus infection", *Immunol Cell Biol* 85: 85-92 2007; Kips J C, et al., "Tumor necrosis factor causes bronchial hyperresponsiveness in rats", *Am Rev Respir Dis* 145: 332-336, 1992; Headley A S, et al., "Infections and the inflammatory response in acute respiratory distress syndrome", *Chest* 111: 1306-1321, 1997). Furthermore, the suppressed production of IL-12 measured in the protected animals likely impaired the activation of some immune cells such as natural killer (NK) cells and cytotoxic $CD8^+$ T cells. Both cell types have been described potentially harmful and involved in immunopathology upon release of inflammatory mediators (La Gruta N L, et al., "A question of self-preservation: immunopathology in influenza virus infection", *Immunol Cell Biol* 85: 85-92 2007). Consistently, IFN-γ production, a hallmark for NK and $CD8^+$ T cell activation, was found significantly lower in the BALFs recovered from the protected animals. In addition, the lower IFN-γ production can affect the neutrophil responses to the virus, including oxidative burst, induction of antigen presentation and chemokine production (Ellis T N and Beaman B L, "Interferon-gamma activation of polymorphonuclear neutrophil function", *Immunology* 112: 2-11, 2004; Farrar M A and Schreiber R D, "The molecular cell biology of interferon-gamma and its receptor", *Annu Rev Immunol* 11: 571, 1993).

Interestingly, a significantly higher number of macrophages were observed in the BALFs of protected BPZE1-treated mice despite lower levels of MCP-1 and GM-CSF, involved in monocytes recruitment and differentiation into macrophages, respectively. However, note should be taken that alveolar macrophages (AM) and not tissue resident macrophages constitute the main macrophage population recovered in the BALFs (Jakubzick C, et al., "Modulation of dendritic cells trafficking to and from the airways", *J Immunol* 176: 3578-3584, 2006). It is thus conceivable that the protected mice can display a reduced macrophage population in their lung tissues compared to infected control mice.

AM have been shown to display suppressive effects on the inflammation reaction by regulating T-cell function (Strickland D H, et al., "Regulation of T-cell function in lung tissue by pulmonary alveolar macrophages", *Immunology* 80: 266-272, 1993), and by suppressing dendritic cells maturation (Holt P G, et al., "Down-regulation of the antigen presenting function(s) of pulmonary dendritic cells in vivo by resident alveolar macrophages", *J Exp Med* 177: 397-407, 1993; Bilyk N and Holt P G, "Inhibition of the immunosuppressive activity of resident pulmonary alveolar macrophages by granulocyte/macrophage colony stimulating factor", *J Exp Med* 177: 1773-1777, 1993; Stumbles P A, et al., "Airway dendritic cells: co-ordinators of immunological homeostasis and immunity in the respiratory tract", *APMIS* 111: 741-755, 2003) and migration to the mesenteric lymph nodes (Jakubzick C, et al., "Modulation of dendritic cells trafficking to and from the airways", *J Immunol* 176: 3578-3584, 2006). One can thus hypothesize that the higher number of alveolar macrophages induced upon influenza challenge contributed to the suppression/control of the inflammation in the protected BPZE 1-treated animals.

Furthermore, we found that the $CD3^+$ T cell population remained unchanged in the protected BPZE1-treated animals upon viral challenge whereas a significant reduction in the proportion of $CD3^+$ T cells was found in the infected control mice. Lymphocyte depletion during highly pathogenic influenza infection has been previously reported (Kash J C, et al., "Genomic analysis of increased host immune and cell death responses induced by 1918 influenza virus", *Nature* 443: 578-581, 2006; Uiprasertkul M, et al., "Apoptosis and Pathogenesis of Avian Influenza A (H5N1) Virus in Humans", *Emerg Infect Dis* 13: 708-712, 2007; Narasaraju T, et al., "Adaptation of human influenza H3N2 virus in a mouse pneumonitis model: insights into viral virulence, tissue tropism and host pathogenesis", *Microbes Infect* 11: 2-11, 2009; Lu X, et al., "A mouse model for the evaluation of pathogenesis and immunity to influenza A (H5N1) viruses isolated from humans", *J Virol* 73: 5903-5911, 1999) and experimental evidences have suggested apoptosis as a potential mechanism (Uiprasertkul M, et al., "Apoptosis and Pathogenesis of Avian Influenza A (H5N1) Virus in Humans", *Emerg Infect Dis* 13: 708-712, 2007; Lu X, et al., "A mouse model for the evaluation of pathogenesis and immunity to influenza A (H5N1) viruses isolated from humans", *J Virol* 73: 5903-5911, 1999). Since no difference in the viral load was observed between protected and non-protected animals, lymphocyte apoptosis can thus not be a direct cytolytic effect of the virus itself Instead, our data are consistent with previous studies which suggested that in H5N 1-infected humans and mice, lymphocyte apoptosis was likely caused by cytokine dysregulation and overactivation of the host immune response (Uiprasertkul M, et al., "Apoptosis and Pathogenesis of Avian Influenza A (H5N1) Virus in Humans", *Emerg Infect Dis* 13: 708-712, 2007; Maines T R, et al., "Pathogenesis of emerging avian influenza viruses in mammals and the host innate immune response", *Immunol Rev* 225: 68-84, 2008). In particular, TNF-α and related TNF-superfamily members including TNF-related apoptosis inducing ligand (TRAIL) are known to induce T cell apoptosis (Simon A K, et al., "Tumor necrosis factor-related apoptosis-inducing ligand in T cell development: sensitivity of human thymocytes", *Proc Natl Acad Sci USA* 98: 5158-5163, 2001; Wang J, et al., "The critical role of LIGHT, a TNF family member, in T cell development", *J Immunol* 167: 5099-5105, 2001). Consistently, lower levels of TNF-α were measured in the BALFs of protected BPZE1-treated mice upon influenza challenge, thus potentially translating into lower T cell apoptosis.

The protective mechanisms responsible for the cross-protection have yet to be identified. However, our data demonstrate that *B. pertussis*-specific adaptive immunity (including cross-reactive antibodies and T cells) is not involved. The observation that live but not dead BPZE1 bacteria confer protection, indicate that bacterial lung colonization, i.e. a prolonged exposure to the host immune system, is necessary to induce the protective mechanism(s). Moreover, induction of the protective mechanisms necessitates more than 3 weeks to develop as mice treated once with live BPZE1 bacteria and challenged 3 weeks later with influenza H3N2 virus were not significantly protected. However, a second BPZE 1 treatment allowed to shorten the time necessary to induce the protective mechanisms and enhance the protection rate, suggesting that some memory cells have been produced upon priming that are capable of responding faster and to a greater extent upon a second encounter with BPZE1 bacteria. Finally, it was observed that three consecutive nasal administrations of live BPZE1 bacteria were necessary to confer 50% protection against human A/PR/8/34 (H1N1) influenza virus. The differential protection rates achieved upon H3N2 and H1N1virus challenge suggest that the molecular disease-mechanisms induced by both viruses are different. However, even though the protection efficiency can vary between subtypes, *B. pertussis* remains a promising universal vaccine against influenza A viruses.

Much of the activity of *B. pertussis* virulence factors is dedicated to immunomodulation so as to suppress, subvert and evade the host defense system (Carbonetti N H, "Immunomodulation in the pathogenesis of *Bordetella pertussis* infection and disease", *Curr Opin Pharmacol* 7: 1-7, 2007). The immune response to *B. pertussis* is initiated and controlled through toll-like receptor (TLR)-4 signaling, inducing the anti-inflammatory cytokine IL-10 production by dendritic cells (DCs) which could inhibit inflammatory responses and limit pathology in the airways (Higgins S C, et al., "Toll-like receptor 4-mediated innate IL-10 activates antigen-specific regulatory T cells and confers resistance to *Bordetella pertussis* by inhibiting inflammatory pathology", *J Immunol* 171: 3119-3127, 2003). Filamentous hemagglutinin (FHA), the major adhesin produced in *B. pertussis*, was shown to stimulate IL-10 production and inhibit TLR-induced IL-12 production by macrophages and DCs, resulting in the development of IL-10 secreting type 1 T-regulatory (Tr1) cells (McGuirk P, et al., "Pathogen-specific T regulatory 1 cells induced in the respiratory tract by a bacterial molecule that stimulates interleukin 10 production by dendritic cells: a novel strategy for evasion of protective T helper type 1 responses by *Bordetella pertussis*", *J Exp Med* 195: 221-231, 2002). Interestingly, the systemic administration of FHA was recently found to reduce intestinal inflammation in a T-cell mediated model of colitis, supporting the anti-inflammatory role of FHA (Braat H, et al., "Prevention of experimental colitis by parenteral administration of a pathogen-derived immunomodulatory molecule", *Gut* 56: 351-357, 2007). However, here no difference in the production of IL-10 and TGF- was found between protected and non-protected mice, ruling out a potential involvement of FHA-mediated induction of Tr1 in the cross-protection against influenza A viruses conferred by *B. pertussis*.

We report here that in a Balb/c mouse model of severe pneumonitis, prior nasal administration of an attenuated strain of *Bordetella pertussis* (BPZE1), the etiologic agent of whooping cough, provided effective and sustained protection against lethal challenge with a mouse-adapted H3N2 influenza A virus and to a lesser extent against human H1N1 (A/PR/8/34) influenza A virus. Although the cellular and molecular players involved in this cross-protection have yet to be identified, our data indicate that *B. pertussis*-specific adaptive immunity and Tr1-mediated down-regulation are likely not involved. Importantly, we found that the cross-protection does not result in viral load reduction. Instead, protected BPZE1-treated mice displayed minimal lung immunopathology, consistent with reduced neutrophil infiltration and lower production of a variety of major pro-inflammatory cytokines and chemokines in their BALFs. Our findings thus strongly suggest that protection against influenza A viruses induced-lethal pneumonitis can be achieved through attenuation of inflammation and dampening of the cytokine storm, and demonstrate the potential use of BPZE1 bacteria as an effective prophylactic means of protecting against virulent influenza A virus infections.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

REFERENCES

1. Carrat F and Flahault A, "Influenza vaccine: the challenge of antigenic drift", *Vaccine* 25: 6852-6862, 2007.
2. Nicholson K G, et al., "Influenza", *Lancet* 362: 1733-1745, 2003.
3. Kash J C, et al., "Genomic analysis of increased host immune and cell death responses induced by 1918 influenza virus", *Nature* 443: 578-581, 2006.
4. Simon A K, et al., "Tumor necrosis factor-related apoptosis-inducing ligand in T cell development: sensitivity of human thymocytes", *Proc Natl Acad Sci USA* 98: 5158-5163, 2001.
5. Kobasa D, et al., "Aberrant innate immune response in lethal infection of macaques with the 1918 influenza virus", *Nature* 445: 319-323, 2007.
6. Tumpey T M, et al., "Characterization of the reconstructed 1918 Spanish influenza pandemic virus", *Science* 310: 77-80, 2005.
7. de Jong M D, et al., "Fatal outcome of human influenza A (H5N1) is associated with high viral load and hypercytokinemia", *Nat Med* 12: 1203-1207, 2006.
8. Beigel J H, et al., "Avian influenza A (H5N1) infection in humans:, *N Engl J Med* 353: 1374-1385, 2005.
9. Uiprasertkul M, et al., "Apoptosis and Pathogenesis of Avian Influenza A (H5N1) Virus in Humans", *Emerg Infect Dis* 13: 708-712, 2007.
10. Peiris J S, et al., "Re-emergence of fatal human influenza A subtype H5N1 disease", *Lancet* 363: 617-619, 2004.
11. Salomon R, et al., "Inhibition of the cytokine response does not protect against lethal H5N1 influenza infection", *Proc Natl Acad Sci USA* 104: 12479-12481, 2007.
12. de Jong M D, et al., "Oseltamivir resistance during treatment of influenza A (H5N1) infection", *N Engl J Med* 353: 2667-2672, 2005.
13. Cook D N, et al., "Requirement of MIP-1 alpha for an inflammatory response to viral infection", *Science* 269: 1583-1585, 1995.
14. Dawson T C, et al., "Contrasting effects of CCR5 and CCR2 deficiency in the pulmonary inflammatory response to influenza A virus", *Am J Pathol* 156: 1951-1959, 2000.
15. Smith D J, et al., "Mapping the antigenic and genetic evolution of influenza virus", *Science* 305: 371-376, 2004.
16. Renauld-Mongenie G, et al., "Induction of mucosal immune response against a heterologous antigen fused to filamentous hemagglutinin after intranasal immunization with recombinant *Bordetella pertussis*", *Proc Natl Acad Sci USA* 93: 7944-7949, 1996.
17. Mielcarek, N, et al., "Nasal vaccination using live bacterial vectors", *Adv Drug Deliv Rev* 51: 55-70, 2001.
18. Mielcarek N, et al., "Intranasal priming with recombinant *Bordetella pertussis* for the induction of a systemic immune response against a heterologous antigen", *Infect immune* 65: 544-550, 1997.
19. Coppens I, et al., "Production of Neisseria meningitidis transferrin-binding protein B by recombinant *Bordetella pertussis*", *Infect immune* 69:5440-5446, 2001.
20. Reveneau N, et al., "Tetanus toxin fragment C-specific priming by intranasal infection with recombinant *Bordetella pertussis*", *Vaccine* 20: 926-933, 2002.

21. Alonso S, et al., "Production of nontypeable haemophilus influenzae HtrA by recombinant *Bordetella pertussis* using filamentous haemagglutinin as carrier", *Infect immune* 73: 4295-4301, 2005.
22. Mielcarek N, et al., "Live attenuated *B. pertussis* as a single-dose nasal vaccine against whooping cough", *PLoS Pathog* 2: e65, 2006.
23. Ho S Y, et al., "The highly attenuated *Bordetella pertussis* BPZE1 strain as a potential live vehicle for the delivery of heterologous vaccine candidates", *Infect Immune* 76: 111-119, 2008.
24. Narasaraju T, et al., "Adaptation of human influenza H3N2 virus in a mouse pneumonitis model: insights into viral virulence, tissue tropism and host pathogenesis", *Microbes Infect* 11:2-11, 2009.
25. Lu X, et al., "A mouse model for the evaluation of pathogenesis and immunity to influenza A (H5N1) viruses isolated from humans", *J Virol* 73: 5903-5911, 1999.
26. Schmitz N, et al., "Interleukin-1 is responsible for acute lung immunopatholoy but increases survival of respiratory influenza virus infection", *J Virol* 79: 6441-6448, 2005.
27. La Gruta N L, et al., "A question of self-preservation: immunopathology in influenza virus infection", *Immunol Cell Biol* 85: 85-92 2007.
28. Kips J C, et al., "Tumor necrosis factor causes bronchial hyperresponsiveness in rats", *Am Rev Respir Dis* 145: 332-336, 1992.
29. Headley A S, et al., "Infections and the inflammatory response in acute respiratory distress syndrome", *Chest* 111: 1306-1321, 1997.
30. Ellis T N and Beaman B L, "Interferon-gamma activation of polymorphonuclear neutrophil function", *Immunology* 112: 2-11, 2004.
31. Farrar M A and Schreiber R D, "The molecular cell biology of interferon-gamma and its receptor", *Annu Rev Immunol* 11: 571, 1993.
32. Jakubzick C, et al., "Modulation of dendritic cells trafficking to and from the airways", *J Immunol* 176: 3578-3584, 2006.
33. Strickland D H, et al., "Regulation of T-cell function in lung tissue by pulmonary alveolar macrophages", *Immunology* 80: 266-272, 1993.
34. Holt P G, et al., "Down-regulation of the antigen presenting function(s) of pulmonary dendritic cells in vivo by resident alveolar macrophages", *J Exp Med* 177: 397-407, 1993.
35. Bilyk N and Holt P G, "Inhibition of the immunosuppressive activity of resident pulmonary alveolar macrophages by granulocyte/macrophage colony stimulating factor", *J Exp Med* 177: 1773-1777, 1993.
36. Stumbles P A, et al., "Airway dendritic cells: co-ordinators of immunological homeostasis and immunity in the respiratory tract", *APMIS* 111: 741-755, 2003.
37. Maines T R, et al., "Pathogenesis of emerging avian influenza viruses in mammals and the host innate immune response", *Immunol Rev* 225: 68-84, 2008.
38. Wang J, et al., "The critical role of LIGHT, a TNF family member, in T cell development", *J Immunol* 167: 5099-5105, 2001.
39. Carbonetti N H, "Immunomodulation in the pathogenesis of *Bordetella pertussis* infection and disease", *Curr Opin Pharmacol* 7: 1-7, 2007.
40. Higgins S C, et al., "Toll-like receptor 4-mediated innate IL-10 activates antigen-specific regulatory T cells and confers resistance to *Bordetella pertussis* by inhibiting inflammatory pathology", *J Immunol* 171: 3119-3127, 2003.
41. McGuirk P, et al., "Pathogen-specific T regulatory 1 cells induced in the respiratory tract by a bacterial molecule that stimulates interleukin 10 production by dendritic cells: a novel strategy for evasion of protective T helper type 1 responses by *Bordetella pertussis*", *J Exp Med* 195: 221-231, 2002.
42. Braat H, et al., "Prevention of experimental colitis by parenteral administration of a pathogen-derived immunomodulatory molecule", *Gut* 56: 351-357, 2007.
43. Menozzi FD, et al., "Identification and purification of transferring- and lactoferrin-binding proteins of *Bordetella pertussis* and *Bordetella bronchiseptica*", *Infect. Immun* 59: 3982-3988, 1991.
44. WHO, "WHO Manual on Animals Influenza Diagnosis and Surveillance" (World Health Organization, Geneva), 2002.
45. Kimman T G, et al., "Development and antigen specificity of the lymphoproliferation response of pigs to pseudorabies virus: dichotomy between secondary B- and T-cell responses", *Immunology* 86: 372-378, 1995.
46. Bao Z, et al., "Glycogen synthase kinase-3beta inhibition attenuates asthma in mice", *Am J Respir Crit Care Med* 176: 431-438, 2007.

What is claimed:

1. A method of lessening the severity of lung immunopathology due to infection with influenza A virus in a mammalian subject who is at increased risk of developing the infection, said method comprising the step of administering to the subject a sufficient amount of a live attenuated, mutated *Bordetella pertussis* strain, wherein the strain comprises a mutated pertussis toxin(ptx) gene, a deleted or mutated dermonecrotic (dnt) gene, and a heterologous ampG gene, and wherein the method elicits an immune response that lessens the severity of the influenza A-induced lung immunopathology in the subject, upon infection with the influenza A virus.

2. The method of claim 1, wherein the strain is administered intranasally.

3. The method of claim 1, wherein at least a first dose and a second dose of the strain are administered to the subject.

4. The method of claim 1, wherein the second dose is administered to the subject one to three weeks from the administration of the first dose.

5. The method of claim 1, wherein the live attenuated, mutated *Bordetella pertussis* strain is BPZE1.

6. The method of claim 1 or claim 5, wherein the infection is with the influenza A virus H3N2.

* * * * *